United States Patent [19]
Thurston et al.

[11] Patent Number: 5,427,094
[45] Date of Patent: Jun. 27, 1995

[54] METHOD AND APPARATUS FOR DETECTING CATARACTOGENESIS

[75] Inventors: George M. Thurston, Belmont; Douglas L. Hayden, Cambridge; Mark S. Bowen, Medford; George B. Benedek, Belmont, all of Mass.

[73] Assignees: Oculon Corporation; Massachusetts Institute of Technology, Cambridge, Mass.

[21] Appl. No.: 149,209

[22] Filed: Nov. 8, 1993

[51] Int. Cl.6 .............................................. A61B 5/00
[52] U.S. Cl. .................................... 128/633; 128/645; 128/653.1; 128/664; 128/665; 607/89
[58] Field of Search ...................... 128/653.1, 633, 645, 128/664, 665; 607/88, 89

[56] References Cited

U.S. PATENT DOCUMENTS

| | | | |
|---|---|---|---|
| 4,350,163 | 9/1982 | Ford, Jr. et al. | 128/633 |
| 4,702,576 | 10/1987 | Magnante | 351/214 |
| 4,854,693 | 8/1989 | Ichihashi et al. | 128/653.1 X |
| 4,957,113 | 9/1990 | Benedek | 128/665 |
| 5,072,731 | 12/1991 | Taratuta et al. | 128/633 |
| 5,203,328 | 4/1993 | Samuels et al. | 128/633 |
| 5,258,788 | 11/1993 | Furuya | 128/633 |
| 5,279,296 | 1/1994 | Thurston et al. | 128/633 |
| 5,318,022 | 6/1994 | Taboada et al. | 128/633 |

FOREIGN PATENT DOCUMENTS 2112171A 7/1983 United Kingdom ........... A61B 3/10
WO92/11799 7/1992 WIPO .......................... A61B 3/117

Primary Examiner—Lee S. Cohen
Assistant Examiner—Brian L. Casler
Attorney, Agent, or Firm—Seed and Berry

[57] ABSTRACT

A method and apparatus for detecting cataractogenesis is disclosed. Quasielastic light scattering data are collected from the lens of an individual to be tested for cataractogenesis. The data are collected from the lens and are processed by an autocorrelator. The data from the autocorrelator are then fit to an autocorrelation function having a component which has a second derivative less than or equal to zero. This autocorrelation function has been found to change predictably with the individual's age and, accordingly, is useful in detecting and determining the degree of cataractogenesis in the individual.

39 Claims, 13 Drawing Sheets

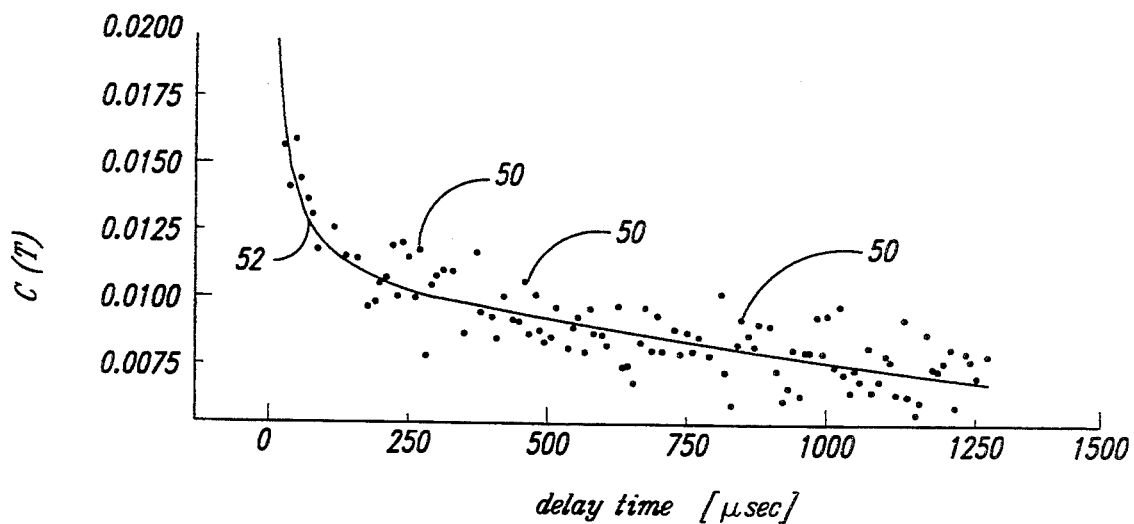
Fig. 2A
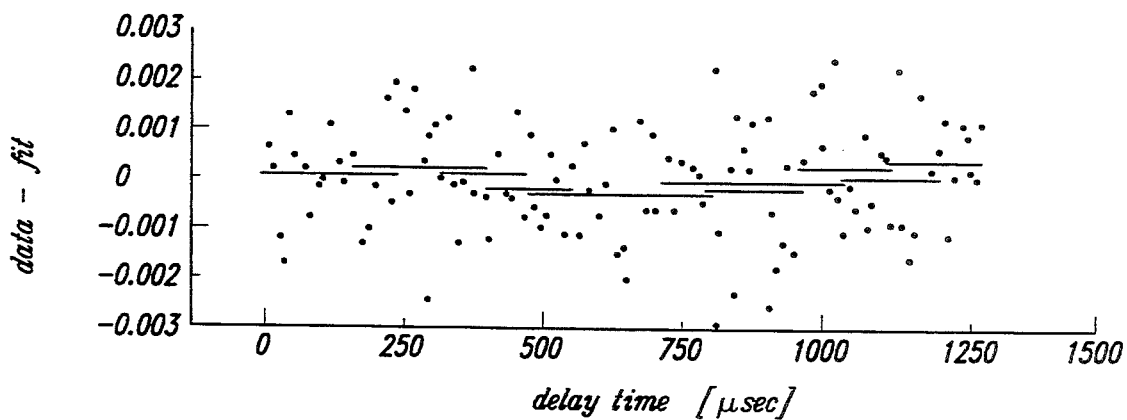
Fig. 2B
*Fit 128 points with 'ocu5'*
*Instrumental weights*
*Converged by ∈ test (∈ = 0.001)*
*−∞ ≤ x ≤ +∞*
$X^2$ = 9.88e-07
base = 0
f = 0.0225 +/- 0.0013
tau_f = 52.1 +/- 8.7
amp_s = 0.706 +/- 0.019
tau_s = 4.9 + 03 +/- 4.4 e + 02
$X^2/^2$ = 0.00959
Intens = 98.5
ResAveMax = 0.00125
DurWatStat = 2.21
Lens =
Loc =
*delayed baseline for fit*
Fig. 2C

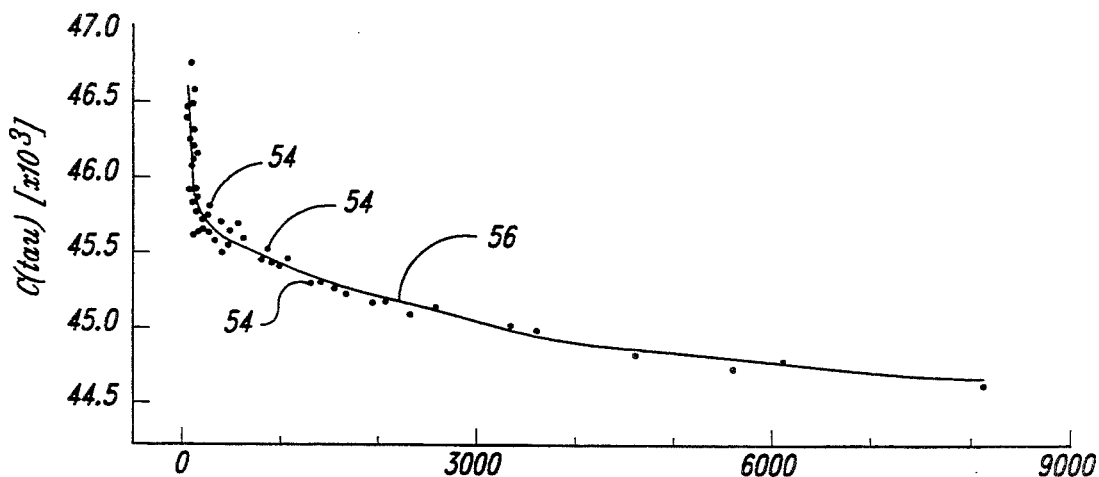
Fig. 3A
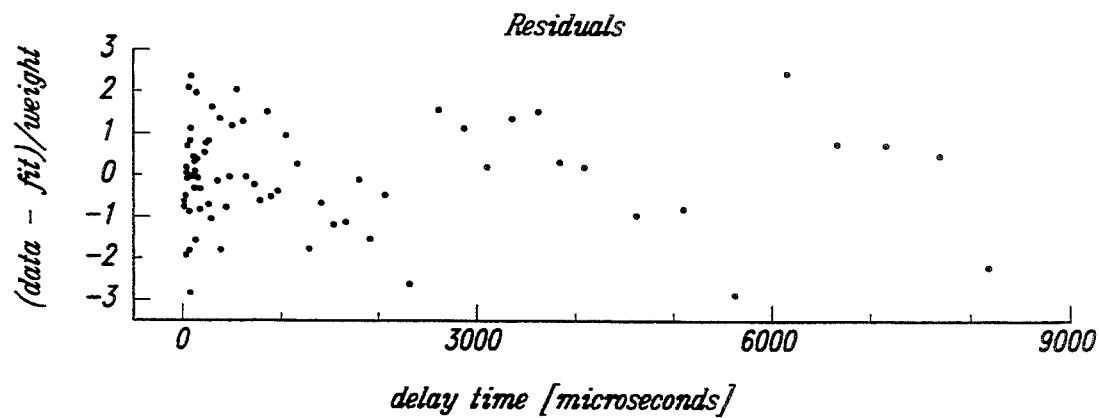
Fig. 3B
*Fit 71 points with 'test 2.5'*
*Instrumental weights*
*Converged by ∈ test (∈ = 0.001)*
$-\infty \leq x \leq +\infty$
$X^2 = 1.554$
$f = 2.2e +03 +/- 1.5e +02$
$as = 0.742 +/- 0.025$
$tauf = 64 +/- 14$
$taus = 6.93e +03 +/- 4.5 +02$
$base = 44539 +/- 27$
$It = 48.08$
$DurWatStat = 1.98$
Fig. 3C

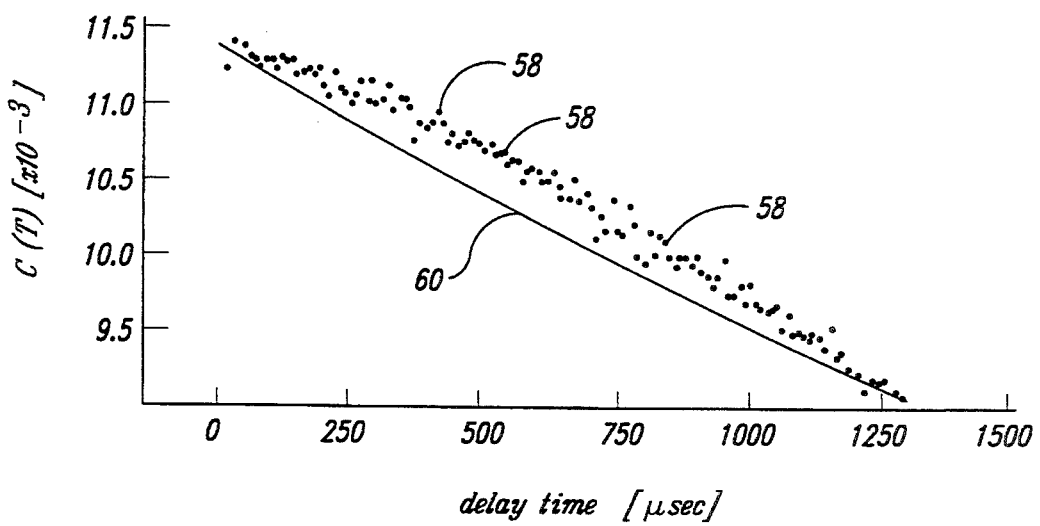
Fig. 4A
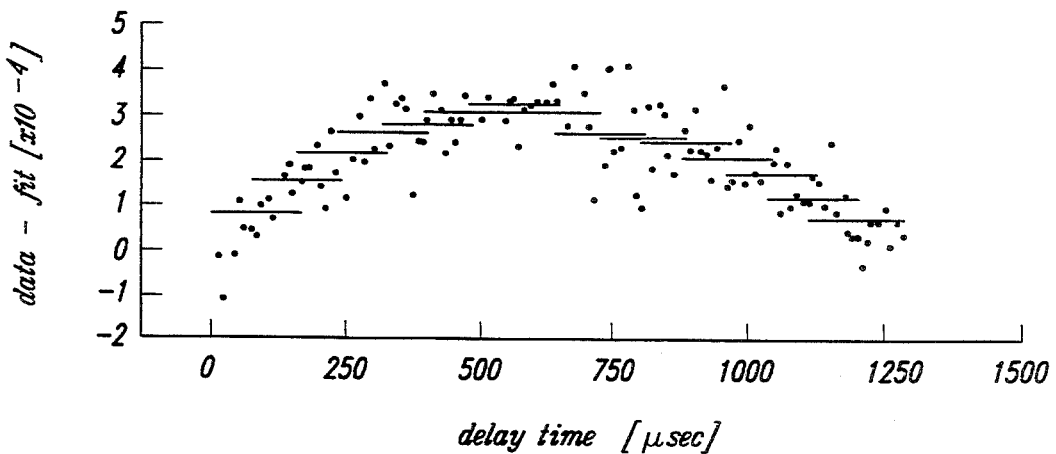
Fig. 4B
*Fit 128 points with 'ocu5'*
*Instrumental weights*
*Fit exceeded iteration limit (20)*
*1 parameter at constrained limit*
$-\infty \leq x \leq +\infty$
$\chi^2 = 5.485e{-}08$
base = 0
f = 0 +/- 0
tau_f = 19.4 +/- 0
amp_s = 1 +/- 0
tau_s = 11324.9 +/- 0
$\chi^2/2 = 0.119$
Intens = 1.47e+03
ResAveMax = 0.218
DurWatStat = 0.151
Lens =
Loc =
*dalayed baseline for fit*
Fig. 4C

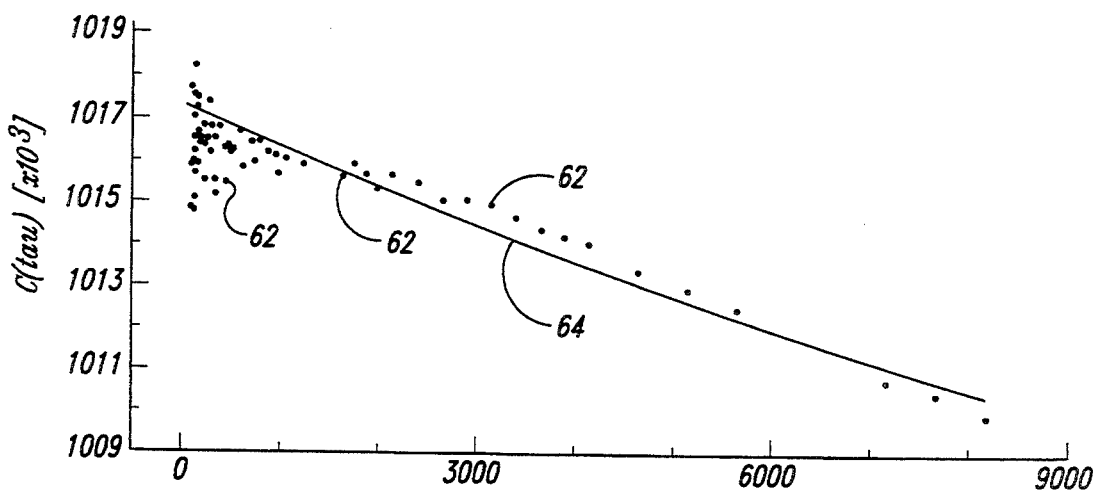
Fig. 5A
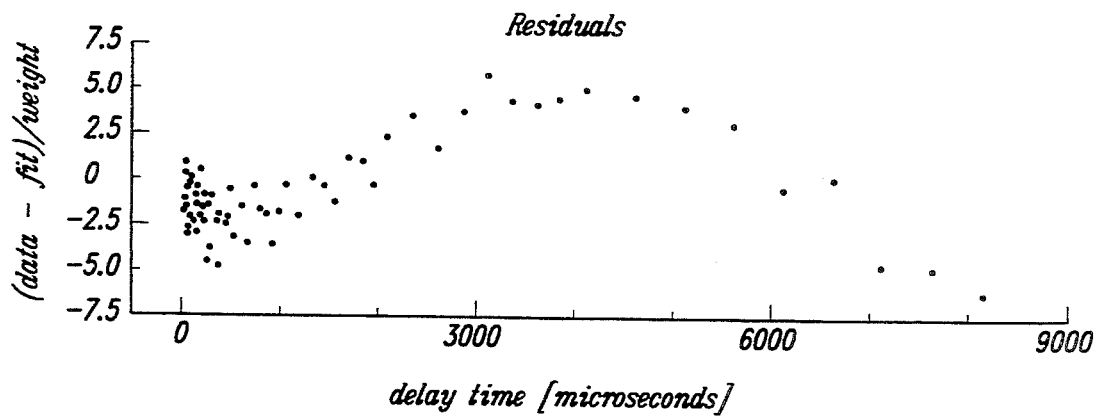
Fig. 5B
*Fit 71 points with 'test 2.5'*
*Instrumental weights*
*Fit exceeded iertion limit (20)*
$-\infty \leq x \leq +\infty$
$X^2 = 7.413$
$f = 29020.6 +/- 0$
$as = 1 +/- 0$
$tauf = 1 +/- 0$
$taus = 58167.9 +/- 0$
$base = 988309 +/- 0$
$It = 231.5$
$DurWatStat = 0.49$
Fig. 5C

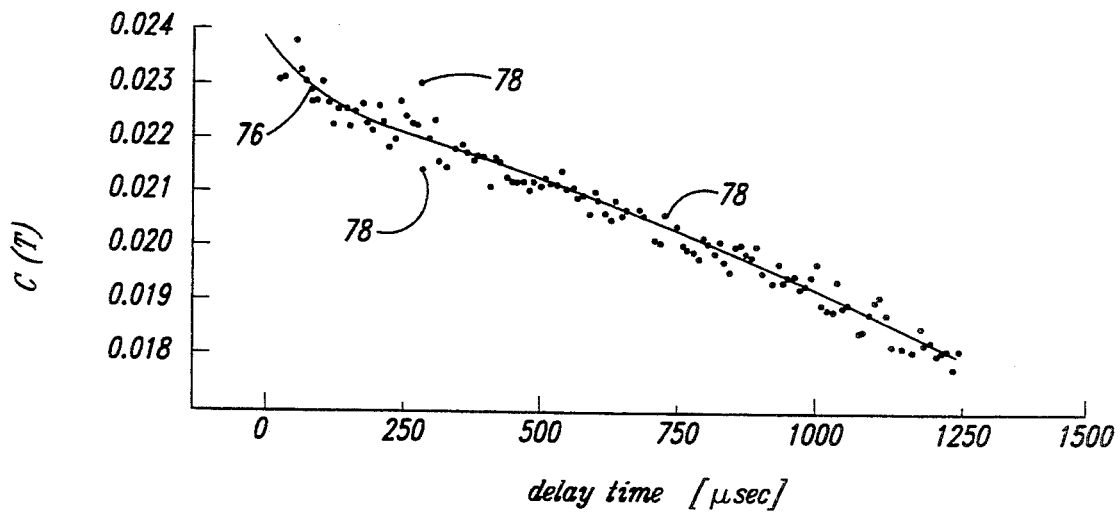
Fig. 11A
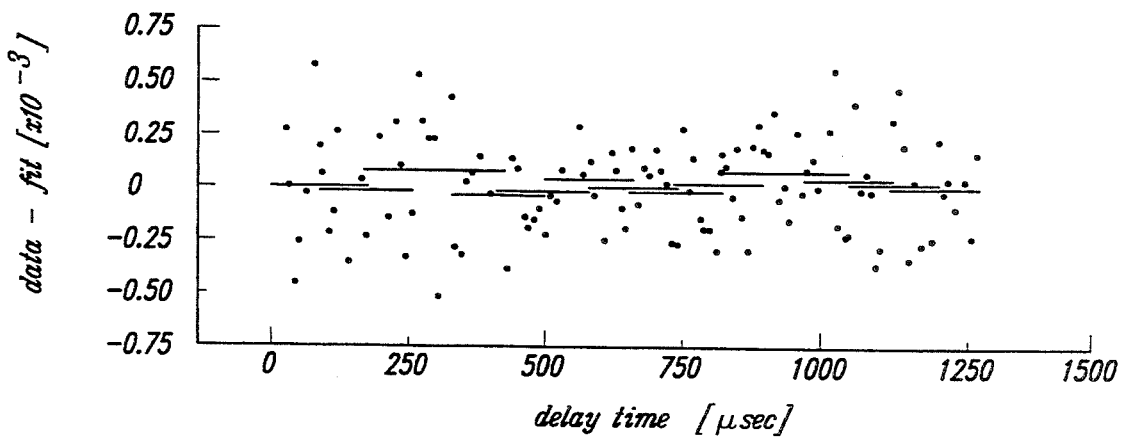
Fig. 11B
*Fit 127 points with 'ocu5'*
*Instrumental weights*
*Fit exceeded iteration limit (20)*
*2 parameters at constrained limits*
$-\infty \leq x \leq +\infty$
$\chi^2 = 4.954\,e-08$
*base = 0*
$f = 0.02 +/- 0.14$
$tau\_f = 76 +/- 81$
$amp\_s = 0.96 +/- 0.29$
$tau\_s = 2\,e+04 +/- 9.8\,e+05$
$h = 0 +/- 0.14\ .0029 => 13\%$
$tau\_c = 0 +/- 1.3\,e+05,\ 59 => 170Hz$
$phi = 0 +/- 33$
$\chi^2/2 = 0.00849$
*Intens = 414*
*ResAveMax = 0.000752*
*DurWatStat = 1.76*
*Lens = od*
*Loc = posterior*
*delayed baseline for fit*
Fig. 11C

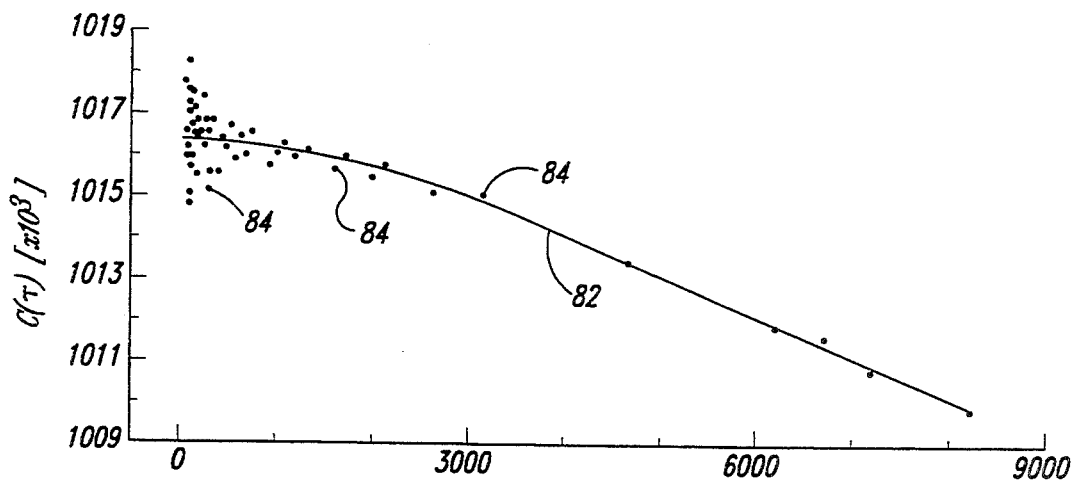
Fig. 12A
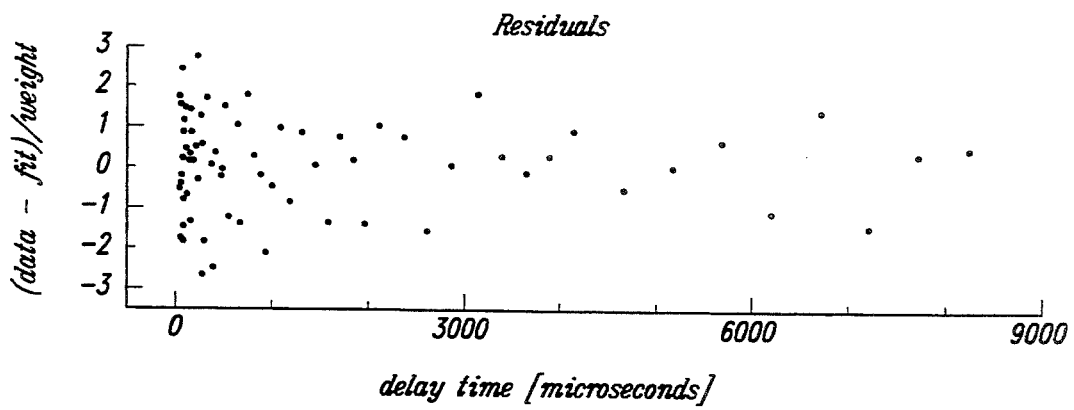
Fig. 12B
Fit 71 points with 'twoexp_cos. 5'
Instrumental weights
Fit exceeded iteration limit (20)
$-\infty \leq x \leq +\infty$
$\chi^2 = 1.435$
$f = 71692.g +/- 6 e +08$
$as = 1$
$tauf = 1$
$taus = 814741 +/- 1.8 e +09$
$base = 941011 +/- 1.6 e +08$
$h = 3726.69 +/- 3.4 e +04$
$tauc = 25694.5 +/- 6.6 e +04$
$It = 231.5$
Calculated Baseline = 943200
Delayed Baseline = 942900
Lens = os
DurWatStat = 2.36
Fig. 12C

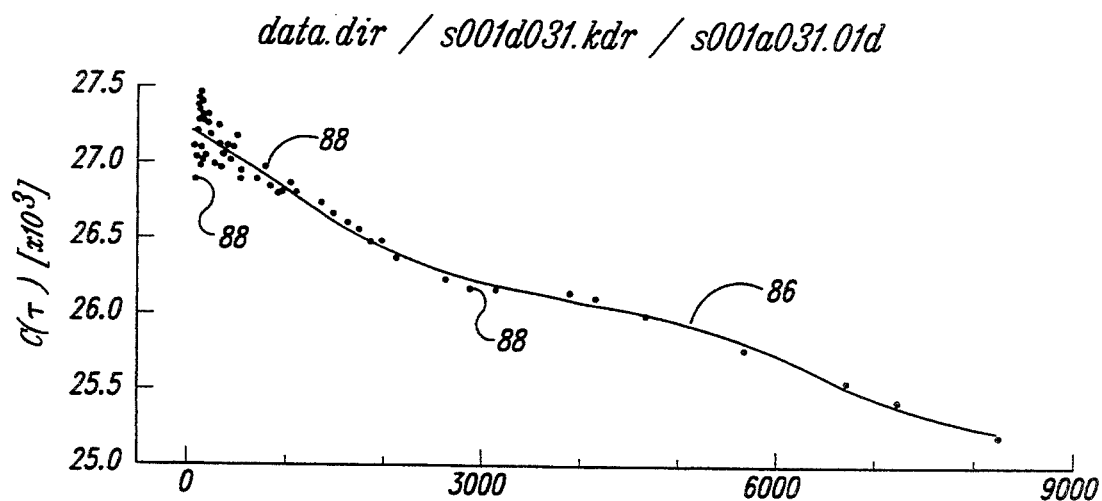
Fig. 13A
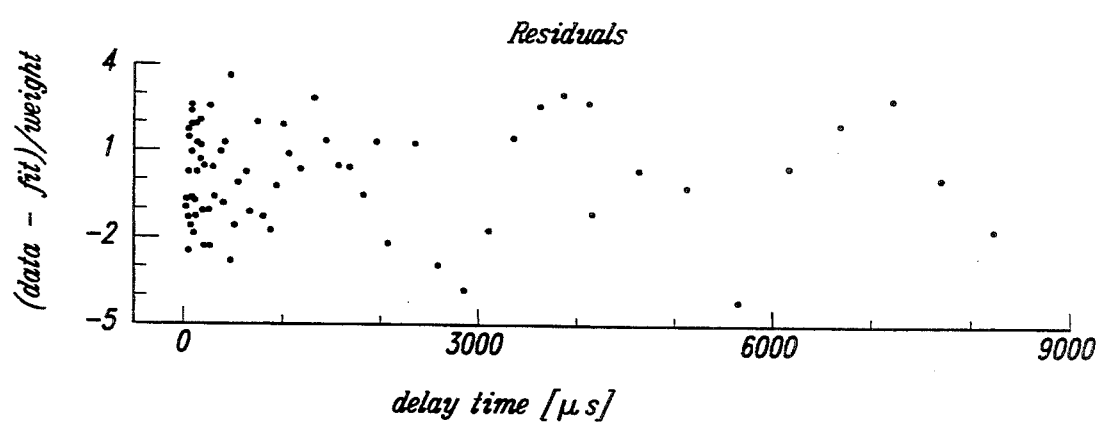
Fig. 13B
*Fit 71 points with 'twoexp_cos. 5'*
*Instrumental weights*
*Fit exceeded iteration limit (20)*
$-\infty \leq x \leq +\infty$
$X^2 = 3.149$
$f = 24989.7 +/- 3.5 \text{ e} +05$
$as = 0.994544 +/- 0.068$
$tauf = 1095.53 +/- 1.7 \text{ e} +03$
$taus = 238282 +/- 3.6 \text{ e} +06$
$base = 2152.06 +/- 3.5 \text{ e} +05$
$h = 79.5644 +/- 18$
$tauc = 5031.52 +/- 1.7 \text{ e} +02$
$It = 33.3g$
Calculated Baseline = 19620
Delayed Baseline = 20560
Lens = od
DurWatStat = 1.60
Fig. 13C

METHOD AND APPARATUS FOR DETECTING CATARACTOGENESIS

TECHNICAL FIELD

The present invention relates to a method and apparatus for cataractogenesis, and more particularly, to a method and apparatus for detecting cataractogenesis by inspecting ocular tissue.

BACKGROUND OF THE INVENTION

A reliable, quantitative and non-invasive method for the characterization of the molecular changes associated with early cataractogenesis in vivo has long been an important goal of human clinical cataract research. Such a method would allow researchers and physicians to (a) assess the effectiveness of putative anticataract reagents; (b) evaluate the cataractogenic role of pharmacological agents or radiation used in the treatment of systematic diseases; (c) characterize early cataract in epidemiological studies of human or animal populations subject to differential cataractogenic stress; and (d) provide a quantitative basis for the medical decision to intervene surgically or pharmaceutically in the treatment of cataract.

In recent years quasielastic light scattering (QLS) has been used to study the ocular lens in vivo and in vitro. A method and apparatus for analyzing QLS is described in U.S. Pat. No. 4,957,113, and U.S. Pat. No. 5,072,731, respectively, which are incorporated herein by reference.

The techniques described in the above-reference patents are capable of quantitating the amount of light scattered by diffusing chemical species in a medium, as well as their rates of diffusion. With QLS, the temporal fluctuations in intensity of light scattered by a selected small volume in the lens which is illuminated by an incident laser beam are studied. The scattered light intensity fluctuates in time because of the Brownian motion of the scattering elements. Brownian motion is defined as the motion of macromolecules caused by thermal agitation and the random striking by neighboring molecules in a solution. In the lens of the human eye, the Brownian motion of protein molecules may be recorded and analyzed by quasielastic light scattering.

Research has shown that the principal scattering elements within the lens are the molecular constituents of the fiber cells. These constituents are principally globular proteins called crystallins. The aggregation of small proteins within the lens is the very first stage in the process of cataractogenesis. As the light scattering becomes more pronounced, it becomes noticeable to the clinician and is termed a cataract. However, this represents a late stage of a continuous process of increase in light scattering with time within the lens. By using information obtained from the light scattered by the various fast and slow moving protein species, it is possible to determine the degree of aggregation and thus the degree of cataractogenesis before it would be noted clinically.

The intensity fluctuations of the scattered light are detected by collecting the light scattered from the illuminated volume in the eye lens and focusing this light onto the surface of an optical square law detector such as a photomultiplier tube or solid-state photodiode. The output of the detector is a photoelectric current whose temporal fluctuations are synchronized with the fluctuations in the scattered light intensity. The temporal fluctuations in the photoelectric current can be mathematically analyzed to provide a quantitative measure of the degree of cataractogenesis.

The experimental data is typically expressed in the form of the temporal autocorrelation function, $C(\tau)$, of the intensity of the detected scattered light from the medium as a function of the delay time, $\tau$. From the mathematical form of the autocorrelation function of the photoelectric current, it is possible to determine the diffusivity of the scattering elements undergoing Brownian movement. The decoded information has been shown clinically to provide an accurate quantitative measure of the source of increased light scattering on a molecular level long before cataract formation could be detected visually by either the subject or the physician.

The QLS inventions described in the above-referenced patents have provided tools to detect cataract formation at a very early stage. However, it has been determined that for certain patients more accurate measurement of the degree of cataractogenesis are desired than be provided existing QLS technology. Therefore, it can be appreciated that there is a significant need for a method and apparatus for detecting cataractogenesis that is applicable to such patients, as well as patients in general. The present invention fulfills this need and provides other related advantages.

SUMMARY OF THE INVENTION

The present invention is embodied in an apparatus and method for detecting cataractogenesis by shining a monochromatic, coherent, collimated light source into the ocular lens. Light scattered by the ocular tissues is collected and analyzed to produce a correlation function as a signature of the cataractogenesis. The signature of the present invention has a component whose second derivative is less than or equal to zero. The degree of cataractogenesis is then determined from the signature.

In one embodiment, an autocorrelation function has a form which contains an exponential component and a nonexponential component. A sinusoidal term may be used as the nonexponential component. A laser may be used as the light source.

The apparatus is embodied in a system that comprises a source of substantially monochromatic, coherent, collimated light, optics to deliver the light to impinge on an ocular lens, a light collector to collect light scattered from the ocular lens, electrical circuitry to perform a correlation analysis to determine a signature indicative of cataractogenesis, the signature having a component whose second derivative is less than or equal to zero, and electrical circuitry to detect cataractogenesis from the signature.

In one embodiment, the electrical circuitry performs an autocorrelation analysis using an autocorrelation function having an exponential and a nonexponential term. A sinusoidal term may be used as the nonexponential term. A laser may be used as the light source. The electrical circuitry fits the data to a curve using the autocorrelation signature having exponential and nonexponential terms. Further electrical circuitry determines the degree of cataractogenesis.

In another embodiment, the collected light is converted into an electrical signal by a square law detector. A photomultiplier tube or a solid-state photodiode may be used. A correlator is used to measure the correlation of the electrical signal produced by the square law detector. A computer may be used to perform the autocorrelation analysis and curve fitting. These and other aspects will be evident upon reference to the following detailed description and attached drawings.

BRIEF DESCRIPTION OF THE DRAWINGS

FIG. 2A is a graph of the data using the instrument of FIG. 1 taken from a human lens in vivo which exhibits a double exponential autocorrelation function.

FIG. 2B is a graph of the residual data resulting from the curve fitting of the data of FIG. 2A to an autocorrelation function containing only exponential terms.

FIG. 2C is statistical data resulting from the curve fitting of the data of FIG. 2A to an autocorrelation function containing only exponential terms.

FIG. 3A is a graph of the data using the instrument of FIG. 1 taken from a human lens in vivo which exhibits a double exponential autocorrelation function.

FIG. 3B is a graph of the residual data resulting from the curve fitting of the data of FIG. 3A to an autocorrelation function containing only exponential terms.

FIG. 3C is statistical data resulting from the curve fitting of the data of FIG. 3A to an autocorrelation function containing only exponential terms.

FIG. 4A is a graph of the data using the instrument of FIG. 1 taken from a human lens in vivo which exhibits non-exponential autocorrelation function.

FIG. 4B is a graph of the residual data resulting from the curve fitting of the data of FIG. 4A to an autocorrelation function containing only exponential terms.

FIG. 4C is statistical data resulting from the curve fitting of the data of FIG. 4A to an autocorrelation function containing only exponential terms.

FIG. 5A is a graph of the data using the instrument of FIG. 1 taken from a human lens in vivo which exhibits a nonexponential autocorrelation function.

FIG. 5B is a graph of the residual data resulting from the curve fitting of the data of FIG. 5A to an autocorrelation function containing only exponential terms.

FIG. 5C is statistical data resulting from the curve fitting of the data of FIG. 5A to an autocorrelation function containing only exponential terms.

FIG. 11A is a graph of the data using the instrument of FIG. 1 taken from a human lens in vivo which exhibits an autocorrelation function with exponential and nonexponential components.

FIG. 11B is a graph of the residual data resulting from the curve fitting of the data of FIG. 11A to the autocorrelation function of the present invention.

FIG. 11C is statistical data resulting from the curve fitting of the data of FIG. 11A to the autocorrelation function of the present invention.

FIG. 12A is a graph of the data using the instrument of FIG. 1 taken from a human lens in vivo which exhibits an autocorrelation function with exponential and nonexponential components.

FIG. 12B is a graph of the residual data resulting from the curve fitting of the data of FIG. 12A to the autocorrelation function of the present invention.

FIG. 12C is statistical data resulting from the curve fitting of the data of FIG. 12A to the autocorrelation function of the present invention.

FIG. 13A is a graph of the data using the instrument of FIG. 1 taken from a human lens in vivo which exhibits an autocorrelation function with exponential and nonexponential components.

FIG. 13B is a graph of the residual data resulting from the curve fitting of the data of FIG. 13A to the autocorrelation function of the present invention.

FIG. 13C is statistical data resulting from the curve fitting of the data of FIG. 13A to the autocorrelation function of the present invention.

DETAILED DESCRIPTION OF THE INVENTION

Figure 1:
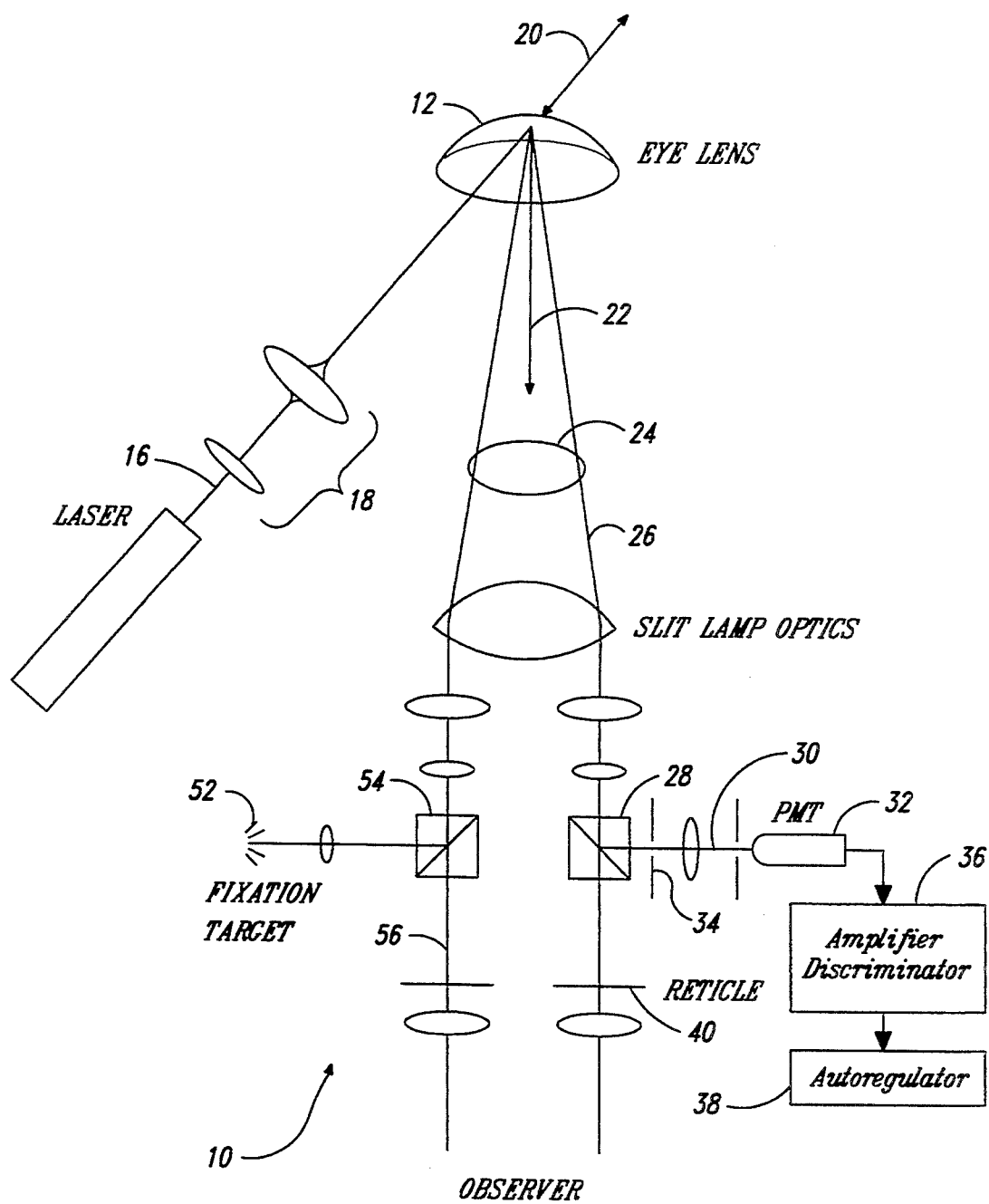
FIG. 1 is a schematic representation of an optical scattering analyzer for the study of light scattered in vivo from the lens of a subject.

The present invention provides an improved apparatus and method for detecting cataractogenesis. A preferred embodiment of the present invention is reflected in an apparatus shown in schematic form in FIG. 1. Referring to FIG. 1, an optical scattering analyzer 10 is used for the study of light scattered in vivo from the lens 12 of a subject. A laser 14 of wave length in the visible range produces a laser beam 16 which is attenuated through conventional optics 18 so as to provide for two incident intensities: one is a maximum intensity of 200 microwatts used for measurement of the autocorrelation function, and the other is a maximum intensity of 40 microwatts used for alignment purposes between measurements. In the presently preferred embodiment the laser 14 is a helium-neon laser that produces monochromatic, coherent collimated light having a wavelength of 632.8 nm. The direction 20 of the laser beam 16 is fixed so as to result in an angle of 140 degrees between the direction 20 of propagation of the laser beam 16 onto the lens 12 and the direction 22 of propagation of the laser light 24 that is scattered by the lens 12. The laser beam 16 is focused to a waist having an approximate diameter of 15–60 microns. Each measurement of the autocorrelation function is conducted within a 5–10 second period. The resulting radiation is well within the guidelines of the American National Standards Institute for ocular exposure.

Within the measurement optical path 26 of the binocular slit lamp, a beam splitter 28 deflects a portion of the scattered light along the direction 22 so as to impinge on the end of a fiber optic 30, which relays the light to a photon-counting photomultiplier tube 32 (such as one manufactured by Hamamatsu). The photon-counting photomultiplier tube 32 produces a corresponding train of pulses. An aperture 34 was used to limit the detected scattering to originate from a portion of the beam which was 200 microns in length in the lens 12. An amplifier-discriminator 36 (such as one manufactured by Malvern Instruments) prepares the pulses produced by the photon-counting photomultiplier tube 32 for input to an autocorrelator 38.

Two different autocorrelators 38 were used in different studies within the United States. In a first experimental setup, the autocorrelator 38 has 128 equally spaced channels and 8 delayed channels, and a sample time of 10 microseconds. The delayed channels are spaced by 10 microseconds starting at delay time 5100 microseconds (5.1 milliseconds). Autocorrelation functions calculated by the autocorrelator 38 are stored in the autocorrelator 38 for later analysis. The first experimental setup uses a measurement period of 10 seconds. In a second experimental setup, the autocorrelator 38 has eight 16 channel correlators to compute the autocorrelation function. The fundamental sample time is 4 microseconds and the dilation factor is two. As is well known in the art, a dilation factor of two indicates that each subsequent set of correlator channels has a sample time that is twice as long as the previous set of correlator channels. Thus, correlator channels 1-16 have a sample time of 4 microseconds, while subsequent correlator channels 17-32 have a sample time of 8 microseconds. The measurement duration is five seconds. The experimental data discussed below provide substantially identical results even though the measurements were made with different autocorrelators. Alternatively, a computer could be used to perform the autocorrelation analysis.

U.S. Pat. No. 4,957,113, and U.S. Pat. No. 5,072,731, respectively, describe an apparatus and method for analyzing QLS data. The data detected by the apparatus is analyzed to determine a signature that is indicative of the degree of cataractogenesis in an individual subject. Subsequent patent applications have described various elements of the signature and have determined additional components of the signature that can be used to determine the degree of cataractogenesis. For example, U.S. Pat. No. 5,279,296, incorporated herein by reference, reports that light scattering is due to both slow and fast diffusing proteins and from immobile scatterers that do not diffuse at all.

In a subsequent U.S. patent application Ser. No. 948,273, filed Sep. 21, 1992, and incorporated herein by reference, it is reported that the cataractogenesis signature can be further determined with the use of a dimensionless parameter, $F_{mos}$, which denotes the fraction of light intensity scattered by mobile scatterers which is associated with slowly moving scatterers. From this application, the double exponential autocorrelation function has the following form:

$$C_N(\tau) = \left(\frac{C(\tau)}{C(\tau_d)}\right) - 1 = \alpha \left[ (1 - F_{mos})e^{-\frac{\tau}{\tau_f}} + F_{mos}e^{-\frac{\tau}{\tau_s}} \right]^2 \quad (1)$$

where $C_N(\tau)$ represents a normalized autocorrelation function that is formed by dividing $C(\tau)$ by a delayed baseline, $C(\tau_d)$, and subtracting one. The term $\alpha$ denotes the observed amplitude to baseline ratio, $\tau_f$ and $\tau_s$ are time constants that characterize the rapidly and slowly diffusing scatterers, respectively, and $F_{mos}$ denotes the fraction of light scattered by mobile scatterers that is associated with slowly diffusing scatterers. It is also possible to normalize the autocorrelation function by dividing by a calculated baseline and subtracting one, and by determining an appropriate baseline by a fitting procedure.

The previous work described above determines a cataractogenesis signature using the following general form of a double exponential autocorrelation function:

$$C_N(\tau) = \alpha \left( \Sigma F_i e^{-\frac{\tau}{\tau_i}} \right)^2 \quad (2)$$

where $C_N(\tau)$ is a normalized autocorrelation function, $\alpha > 0$ is the observed amplitude to baseline ratio, $0 \leq F_i \leq 1$ represents the fraction of light intensity scattered by each mobile diffusing species, i, and $\tau_i$ is the time constant that characterize the mobile scatterers. In equation (2), it is understood that the sum of all $F_i$ equals 1. It is evident that $C_N(\tau)$, as given in equation (2) above, must satisfy the following equation:

$$\frac{d^2 C_N}{d\tau^2} > 0 \quad (3)$$

over all finite ranges of delay times.

As seen in FIG. 2A, the autocorrelation function is represented by a series of discrete data points 50. A curve, $C_{fit}(\tau)$, indicated by the reference numeral 52, representing the autocorrelation function of equation (2) is determined by a curve fitting program. Any one of a number of well known curve fitting algorithms can be successfully applied to the discrete data points 50. One example of such an algorithm is the Marquardt nonlinear least squares algorithm (P.R. Bevington, *Data Reduction and Error Analysis for the Physical Sciences*, McGraw-Hill, New York, 1969, Chap. 11). The curve fitting can be performed by a computer.

The data shown in FIGS. 2A-2C were computed using the first experimental setup described above with a serial correlator of 128 channels spaced ten microseconds apart and a total measurement duration of ten seconds. Eight delayed channels starting at 5,100 microseconds are used to estimate a delayed baseline.

The accuracy of the curve fitting program can be determined by a number of different techniques. The residual data from the curve fitting program is plotted in FIG. 2B using the formula $R(\tau) = C_N(\tau) - C_{fit}(\tau)$. The residual data in FIG. 2B is randomly distributed about zero, indicating a good fit. If the residual data has a pattern, it indicates that the form of equation (2) has not provided a good fit to the discrete data points 50 (see FIG. 2A). The term "good fit" as used herein, refers to mathematical measures of the preciseness with which a curve is fit to the measured data points.

Another form of statistical analysis can also be used to determine the accuracy of the curve fitting program. The Durbin-Watson statistic is a well known statistic used in data analysis. Applications of the Durbin-Watson statistic are discussed in J. Neter, W. Wasserman, and M. H. Kutner, *Applied Linear Statistical Models*, Irwin, Homewood, Ill., 1985, Chap. 13. The particular form of the Durbin-Watson statistic developed for the present invention is applied to the residual data $R(\tau)$ using the following formula:

$$DW\_stat = \frac{\sum\limits_{i=2}^{128} (R(\tau_i) - R(\tau_i - 1))^2}{\sum\limits_{i=1}^{128} (R(\tau_i))^2} \quad (4)$$

where the subscript "i" refers to successive channels of the observed autocorrelation function, and DW_stat is a measure of the extent of correlation of successive residuals in the fitted autocorrelation function. The form of equation (4) applies to a correlation function obtained using 128 channels as described above; with other correlation function setups a similar equation would apply with different limits of summation. A value of DW_Stat near two indicates no correlation of successive residuals (which is the desirable circumstance for a curve that provides a good fit for a particular autocorrelation function), while a value of zero for DW_stat indicates perfect correlation. The statistics shown in FIG. 2C are the results of the analysis of the autocorrelation function of FIG. 2A and the residual data in FIG. 2B. As seen in FIG. 2C, the DW_stat has a value of 2.21, indicating that the autocorrelation function represented by the curve 52 of FIG. 2A is a good fit to the discrete data points 50. Thus, the autocorrelation function of equation (2) can produce a curve with a good fit for this particular patient.

Similar results are obtained in the second experimental setup described above with a different autocorrelator having eight 16 channel correlators. The fundamental sample time was 4 microseconds and the dilation factor was two. The measurement duration was five seconds. The model equation used for the analysis of the resulting autocorrelation is given by:

$$C(\tau) = \alpha B \left[ (1 - F_{mos})e^{-\frac{\tau}{\tau f}} + F_{mos}e^{-\frac{\tau}{\tau s}} \right]^2 + B \qquad (5)$$

where $B > 0$ is a baseline value and in which $0 \leq F_{mos} \leq 1$. As with the autocorrelation functions of equations (1) and (2), the form of $C(\tau)$ in equation (5) also has a second derivative which is greater than zero. In equation (5), the autocorrelation function was not normalized. Instead, appropriate values for the baseline, B, were determined in the curve fitting process. The data shown in FIGS. 3A-3C was collected using the second experimental setup. The discrete data points 54, as well as a curve, $C_{fit}(\tau)$, indicated by the reference numeral 56, are shown an FIG. 3A. The curve 56 is determined by the curve fitting program using equation (5).

As seen in the residual data of FIG. 3B and the statistics of FIG. 3C, the curve 56 is a good fit to autocorrelation function of equation (5). The residual data is randomly distributed about zero, and the DW_stat is 1.98. Thus, the double exponential form of the autocorrelation function illustrated in equations (2) and (5) can have utility even with different equipment and measurement parameters.

Although the double exponential autocorrelation function illustrated by equations (2) and (5) produces useful results in almost all circumstances, there are subjects for whom the double exponential autocorrelation function does not produce curves with a particularly good fit. For example, the discrete data points 58 in FIG. 4A are fitted to a curve, $C_{fit}(\tau)$, indicated by the reference numeral 60, by the curve fitting program. These data are obtained using the first experimental setup described above with a serial correlator of 128 channels spaced ten microseconds apart and a total measurement duration of ten seconds. Eight delayed channels starting at 5,100 microseconds are used to estimate a delayed baseline. Although the curve 60 appears to be almost a straight line, the curve fitting program uses equation (1). The residual data, shown in FIG. 4B shows a definite pattern instead of random distribution about zero, indicating that the curve 60 of FIG. 4A is not a particularly good fit for the autocorrelation function of equation (2). Furthermore, the DW_stat, shown in FIG. 4C, has a value of 0.151, indicating that the curve 60 and the form of equation (2) do not produce as precise as desired results for the discrete data points 58.

Similarly, the double exponential autocorrelation function illustrated by equation (5) does not provide a curve with a particularly good fit for the data shown in FIG. 5A. The data in FIGS. 5A-5C was obtained using the second experimental setup described above with an autocorrelator having eight 16 channel correlators. The fundamental sample time was 4 microseconds and the dilation factor was two. The measurement duration was five seconds. The model functional form used to fit the observed autocorrelation functions is given by equation (5). As seen in FIG. 5A, a curve, $C_{fit}(\tau)$, indicated by the reference numeral 64, is derived from the discrete data points 62 using the curve fitting program and the double exponential autocorrelation function of equation (5). The residual data shown in FIG. 5B shows a definite pattern, indicating that curve 64 of FIG. 5A is not a good fit for the autocorrelation function of equation (5). In addition, the DW_stat, shown in FIG. 5C, has a value of 0.49, indicating that there is a strong correlation between successive residual data points. Thus, the double exponential form of equation (5) may not always produce a curve with a fit as precise as desired.

The observed autocorrelation functions shown in FIGS. 4A and 5A cannot be fit as precisely as is desirable using any model functional form having a second derivative that always satisfies equation (3), that is, a second derivative which is always positive for any value of $\tau$.

The present invention results from analyzing the influence of motion of a scattering medium on the temporal autocorrelation function $C(\tau)$ of the intensity of the scattered light.

To understand the origin of the present invention, consider first the case of a stationary medium, which contains diffusing light scattering elements such as the small and large protein particles of the ocular lens. At a given starting time t those particles or scattering elements which are illuminated by the incident light beam, and which are also within the volume in space from which the scattering is detected by the instrument (herein called the "scattering volume"), will have a particular set of relative positions and orientations. This set of positions and orientations largely governs the intensity of the light scattered in any particular direction, as is well known. As the particles or scattering elements diffuse, these relative positions and orientations change with time. As a result, the amount of light scattered changes with time, and gradually becomes successively more uncorrelated with its initial value. As is well known, a useful statistical measure of this correlation and its decrease with time $\tau$ following an initial time t is the temporal autocorrelation function $C(\tau)$, which may be defined as $$C(\tau) = [\text{limit for large } T] \frac{1}{T} \int_0^T I(t)I(t + \tau)dt \qquad (6)$$

in which T denotes the total time of measurement and $\tau$ is much less than T. As is also well known, in the case of particles undergoing Brownian motion or of other light scattering entities which obey a diffusion equation, the decrease of the function $C(\tau)$ as a function of delay time $\tau$ is in general characterized by decreasing exponential functions. In such a case the appropriately normalized form of the autocorrelation function will be as given above in equation (2). In this case the source of the loss of correlation of the intensity with itself, as a function $\tau$, is the diffusion of the particles relative to one another.

The present invention identifies a source of the dependence of $C(\tau)$ on $\tau$ in the ocular lens, aside from the diffusion of particles as described above. This source stems from the fact that in general, unless the eye is completely immobilized, it executes continual small motions even when a subject is asked to gaze at a very small fixation target. The consequent motion of the living eye and the instrument relative to one another will result in successive occupation of the scattering volume V by somewhat different portions of the ocular lens. Accordingly, we use $\Omega(t)$ to denote that portion of the ocular lens which lies within the scattering volume at time t.

Figure 6A:
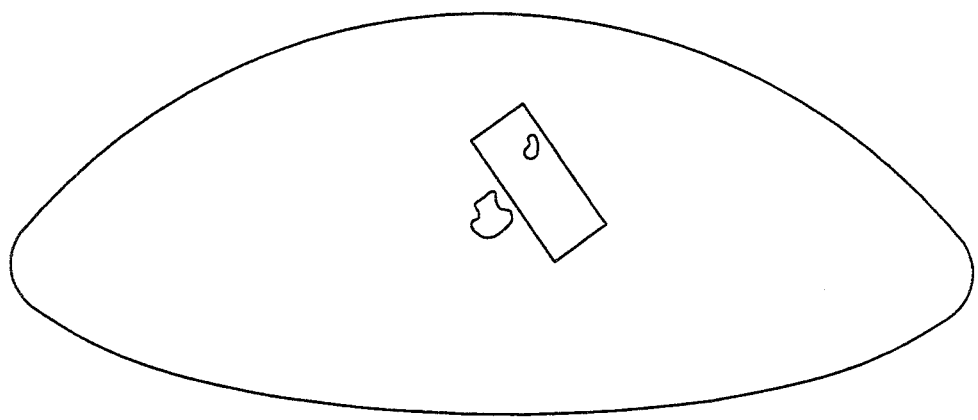
FIG. 6A depicts the scattering volume at one point in time.
Figure 6B:
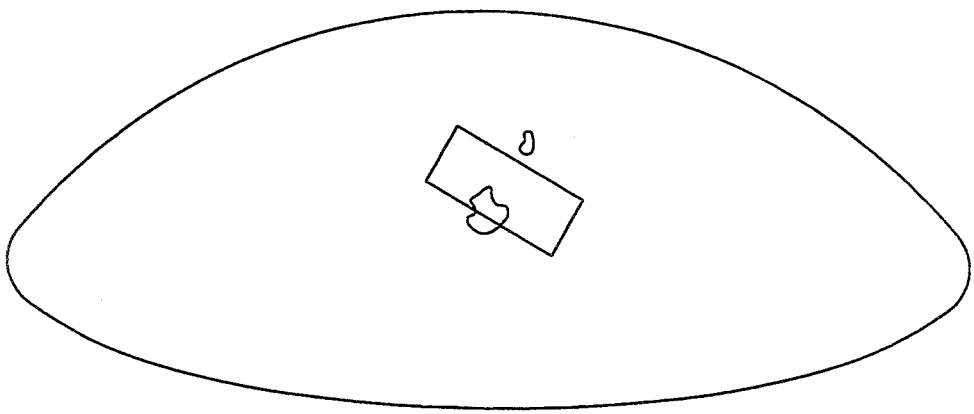
FIG. 6B depicts the scattering volume of FIG. 6A at subsequent point in time.

This principle may be best illustrated in FIGS. 6A and 6B. In FIG. 6A, the lens is in a first position at time, t, such that the scattering volume, V, has scattering elements having a particular identity, $\Omega$. At a subsequent point in time, $t+\tau$, the scattering volume, V, will have a different identity, $\Omega'$, unless $\Omega$ and $\Omega'$ have the same identity. Thus, the change in identity of the scattering volume, V, over time can cause a fluctuation in the intensity of the scattered light.

When the identity $\Omega$ of the material within the scattering volume V does vary with time t, two physical reasons can be identified which can alter the dependence of $C(\tau)$ on $\tau$ from what would be observed due solely to diffusive motion within a fixed volume $\Omega$.

(i) The first reason is that the ocular lens is spatially heterogeneous with respect to its ability to scatter incident light. That is, different portions of the ocular lens scatter different amounts of light. Therefore, the time average intensity $<I>(\Omega)$ scattered from an ocular lens volume $\Omega$ will in general be different from that corresponding to an ocular lens volume $\Omega'$, $<I>(\Omega')$, unless $\Omega$ and $\Omega'$ are identical.

Now, if $\Omega$ were fixed, and if there were no motion of the scattering elements within the scattering volume, I(t) would be a constant with time, and as a result $C(\tau)$ would be constant, from equation (6).

In contrast, consider the situation in which there is assumed to be no motion of the scattering elements relative to the lens material, but $\Omega$ and $<I>(\Omega)$ change with time. Then $C(\tau)$ will depend on $\tau$ through $$C(\tau) = [\text{limit for large } T] \frac{1}{T} \int_0^T <I> [\Omega(t)] <I> [\Omega(t+\tau)] dt \quad (7)$$

in which the brackets '[]' and '()' denote functional dependence. The greater the amplitude of eye motion, the greater the extent to which $\Omega$ and hence $<I>(\Omega)$ will change with time, and the greater the extent to which $C(\tau)$ will be altered from the $\tau$ dependence which would result from diffusive motion alone. For a given amplitude of eye motion, the greater the variation of the intensity $<I>$ with position in the lens, the greater the extent to which $C(\tau)$ will be altered, as well.

This latter relationship means that $C(\tau)$ measured in the presence of eye motion can potentially provide a useful measure of the degree of spatial heterogeneity of scattering within the lens.

(ii) The second reason may be described by considering a limiting case which contrasts with that described in paragraph (i) above. Consider a situation in which (a) $<I>$ does not vary significantly from place to place within the portion of the ocular lens being measured, (b) $\Omega$ is a function of time, and (c) there is diffusive motion of the light scattering elements within the ocular lens, and in turn within each volume $\Omega$. In this case the reasons for the variation of $C(\tau)$ given in paragraph (i) above do not apply, since $<I>$ does not vary with position.

There is nevertheless another reason for variation of $C(\tau)$ from the form which would apply due to diffusion alone in the absence of motion. This reason stems from the fact that at any given time, t, the actual intensity of the scattered light, I(t), will in general differ from its time average value $<I>$, because of the motion of the scattering elements. As is well known, I(t) is determined by the vector positions of all of the scattering elements which are in the scattering volume, relative to one another. More specifically, let $\{r_i(t)\}$ denote the set of vector positions of scattering elements, labeled by index i, in space at time t. In this context the set $\Omega(t)$ can be regarded as the set of all indices i which correspond to scattering elements in the scattering volume V at time t. I(t) can then be written as a function of the set of vector displacements, $\{r_i(t)-r_j(t)\}\Omega(t)$, in which the indices i and j range only over those scattering elements in V at time t. As noted above, the change with time of these relative positions is the reason for the variation of I(t) with time due to diffusion alone, and the consequent variation of $C(\tau)$ with $\tau$.

As the eye moves, however, and $\Omega$ changes, different scattering elements i will be found within V at time $t+\tau$, than were found in V at time t. This gives rise to a new set $\{i,j\}$ of pairs of indices i and j, which determine the relevant displacements $\{r_i(t+\tau)-r_j(t+\tau)\}\Omega(t+\tau)$, and which in turn determine $I(t+\tau)$.

As an extreme example, if after a characteristic delay time $\tau_{motion}$ the volumes $\Omega(t)$ and $\Omega'(t+\tau_{motion})$ have no overlap, the sets of pairs of indices contributing to the scattering, $\{i,j\}$ will be completely different at the two times, provided that no individual scatterer within $\Omega$ has yet diffused from $\Omega$ to $\Omega'$ or otherwise affected $\Omega'$, and vice versa. Under these conditions, the intensities $I(\Omega)$ and $I(\Omega')$ will be uncorrelated, and therefore $$C(\tau=\tau_{motion}) = <I>^2 \quad (8)$$

On the other hand, if the $\tau$ dependence of $C(\tau)$ were due solely to diffusion of a single species of scattering element in the absence of overall eye motion, $C(\tau)$ would take the following form well known in the art:

$$C_{diffusion}(\tau) = \alpha <I>^2 \exp\left[\frac{-2\tau}{\tau_{diffusion}}\right] + <I>^2 \quad (9)$$

in which $0 < \alpha < 1$. It may readily be seen by comparison of equations (8) and (9) that if $\alpha <I>^2 \exp[-2\tau_{motion}/\tau_{diffusion}]$ is measurably different from $<I>^2$, equation 9 is incompatible with equation (8), and equation (9)

would, in such a case, be incorrect. This analysis makes it evident that in the presence of eye motion, even with no intrinsic spatial variation of the intensity, $C(\tau)$ can be quite different from the functional form due to diffusion alone, and that two physically important time scales relevant for evaluating the influence of eye motion on $C(\tau)$, in the absence of spatial heterogeneity of $<I>$, are $\tau$motion and $\tau$diffusion.

The situation in practice may involve a mixture of the reasons described in paragraphs (i) and (ii) for the influence of eye motion on $C(\tau)$. This would occur, for example, for diffusing scatterers in the lens whose concentration varied with position, or which were present together with a spatially varying background intensity due to relatively immobile scatterers. The time varying identity of the diffusing scatterers would give rise to variation of $C(\tau)$ due to motion according to reason (ii) above, while the spatial variation of the intensity due either to immobile scatterers or to a concentration gradient of diffusing scatterers would give rise to variation of $C(\tau)$ as described in paragraph (i) above. The presence of such spatial variation may be readily appreciated from the disclosure given in U.S. Pat. No. 5,279,296, and U.S. patent application, Ser. No. 948,273, filed Sep. 21, 1992.

With the foregoing reasoning it can be readily understood that $C(\tau)$ can differ from the form expected due to diffusion, in the presence of significant eye motion, or in the presence of eye motion in combination with spatial heterogeneity of the intensity of light scattered from the lens.

In particular, the form of this new spatial variation can be such that $C(\tau)$ can exhibit a second derivative which is not positive. This can be seen by considering a special case of reason (i), given above, for the variation of $C(\tau)$ in the presence of motion.

In particular, we consider a sinusoidal rotational motion of the eye around a single axis in space, the relevant angular displacement from the origin of $\theta$ being given by $\theta(t)$. That is, we let $\theta = \theta_o \sin(2\pi t/\tau_c) + \phi$, in which $\theta_o$ denotes the angular amplitude of the motion, $\tau_c$ denotes its period, and $\phi$ denotes its phase. In general such motion will give rise to a corresponding sinusoidal motion of the lens material through the scattering volume V. The average scattered intensity $<I>$ will now be a function of time through its dependence on $\theta$.

To investigate the consequence of this dependence in a simple case, we first expand $<I>(\theta)$ in a power series about the position $\theta = 0$:

$$<I>(\theta) = <I>(0) + \frac{d<I>}{d\theta} \theta + \ldots, \qquad (10)$$

in which the derivative is evaluated at $\theta = 0$.

We now substitute $\theta = \theta_o \sin(2\pi t/\tau_c) + \phi$ into equation 10 to obtain an expression for $<I>(t)$, further substitute the resulting expression for $<I>(t)$ into equation (7) and perform the indicated integration and limiting process. To carry this out it is convenient to let $A = (2\pi t/\tau_c) + \phi$ and $B = (2\pi\tau/\tau c)$, c), and to use the identity $\sin A \sin (A+B) = \sin^2 A \cos B + (\frac{1}{2})\sin 2A \sin B$. One readily obtains $$C(\tau) = [<I>(0)]^2 + \left(\frac{1}{2}\right)(\theta_o)^2 \left[\frac{d<I>}{d\theta}\right]^2 \cos\left(\frac{2\pi\tau}{\tau_c}\right), \qquad (11)$$

in which we have for convenience dropped all terms in equation (10) beyond those which are shown; that is, we assume a purely linear dependence of $<I>$ on $\theta$ for the present purpose of illustration.

Thus, the present analysis provides an explicit example of motion of the eye which can give rise to a function $C(\tau)$ having terms with a negative second derivative. In many respects the present example is the simplest to be expected, for two reasons. First, in general the angular position of an eye for which the gaze is fixed will vary somewhat with time about the fixed target position. A sinusoidal variation is a simple model of such a variation. Second, in general the average intensity $<I>$ will vary to some degree with position, and for small enough displacements such variation will be linear with position. This analysis predicts that functional forms like those given in equation (11) will be found in intensity autocorrelation functions obtained from the lens of the eye.

The present analysis can clearly be generalized as follows: (1) more terms could be considered in the power series of equation (10), (2) more complicated dependencies of $<I>$ on $\theta$, such as a sharp spike in the intensity near a particular value of $\theta$, could be considered directly, proceeding in a manner similar to that above, (3) different and more complicated dependencies of $\theta$ on t could be considered, (4) other degrees of freedom of eye motion besides $\theta$ could be considered, and (5) some combination of (1), (2), (3) and/or (4) could be considered. In each case it is readily seen that contributions to $C(\tau)$ which are not of an exponential nature, as occurred in equation (11), could readily arise. It should also be realized that in the case of eye motion in which $\theta$ (t) varied so as to have an exponential dependence of $<\theta(t)\theta(t+\tau)>$ on delay time, exponential correlation of the intensity could also arise due to eye motion.

Equation (11) shows explicitly that both the spatial heterogeneity of scattering, represented by the factor $$\frac{d<I>}{d\theta},$$

and the amplitude of eye motion, as represented by the factor $(\theta_o)^2$, contribute to the influence of motion on the correlation function. This raises the possibility that one could determine the factor $$\frac{d<I>}{d\theta}$$

by examination of $C(\tau)$ and thereby obtain a measure of the spatial heterogeneity of scattering from the lens. As this heterogeneity is known to increase in cataract formation, such an analysis can provide an additional quantitative tool with which to characterize the process of cataractogenesis.

We note that for the correlation function form given in equation (11), there are ranges of $\tau$, namely the open intervals $0 < \tau < (\frac{1}{2})\tau_c$, $\tau_c < \tau < (3/2)\tau_c$, $2\tau_c < \tau < (5/2)\tau_c$, and so forth, within which $$\frac{d^2C}{d\tau^2} < 0$$

Thus the functional form given in equation (11) shows that for the simplest consideration of eye motion, terms are expected to contribute to $C(\tau)$ which have negative second derivative with respect to $\tau$. Such terms do not arise in the form of C(τ) due to diffusion alone, as noted above.

The present invention uses an autocorrelation function C(τ) having a component whose second derivative satisfies the following equation:

$$\frac{d^2C}{d\tau^2} \leq 0 \tag{12}$$

over some range of τ. That is, the second derivative of the component of the autocorrelation function is less than or equal to zero over some range of τ. This allows an autocorrelation function to fit the discrete data points 58 and 62, shown in FIGS. 4A and 5A, respectively. The present invention uses an autocorrelation function that includes both a double exponential component and a nonexponential component which satisfies equation (12) over at least a portion of the delay times τ. The autocorrelation function of the present invention also permits the analysis of discrete data points 50 and 54, shown in FIGS. 2A and 3A, respectively as did the previous model function. Thus, the present invention extends previous techniques to permit analysis of autocorrelation functions in a number of patients for whom previous model functions did not fit the data as precisely as desired.

As noted above, the intensity of the light scattered from the ocular lens increases with time, and eventually is designated clinically as the phenomenon of cataract. We have found that the occurrence of nonexponential correlation functions is in fact related to the intensity of light scattered from the lens. This underscores the utility of the nonexponential correlation functions. This relationship is demonstrated by FIG. 6. The data shown in FIG. 6 was obtained from a population of 208 volunteers in a study of the dependence of C(τ) on age and location within the ocular lens. One of the measured quantities is the total intensity of the scattered light, $I_{tot}$, which is shown on the horizontal axis in units of thousands of photons detected per second (kHz). For each lens, the observed correlation functions in the posterior cortex were divided into two categories: (1) functions with a good fit using an autocorrelation function having only a double exponential component, and (2) autocorrelation functions having a nonexponential component. The average values of the intensity, $<I_{tot}>_1$ and $<I_{tot}>_2$ within each category were computed for each lens. Note that all of the functions for some lenses would fall in category (1), all of the functions for other lenses would fall in category (2), and some lenses could yield both types of functions. Thus, some lenses would not be classified in a given category if corresponding correlation functions of that type had not been observed.

The cumulative density functions, $CDF(<I_{tot}>_1)$ and $CDF(<I_{tot}>_2)$ were then computed. $CDF(<I_{tot}>_i)$ is defined as in the standard statistical practice, as the fraction of the observed average values, within category i, which are less than or equal to $<I_{tot}>_i$. It is clear that the distribution of average intensities for the autocorrelation function with a nonexponential term is shifted to significantly higher intensities than the corresponding distribution for the double exponential correlation functions. In particular, the mean value is 522 kHz for autocorrelation functions having a nonexponential component, and only 209 kHz for double exponential autocorrelation functions. No averages for double exponential functions exceeded 750 kHz, while numerous autocorrelation functions having a nonexponential component exhibited average values beyond 750 kHz, ranging up to 1800 kHz. In fact, the lens exhibiting the 1800 kHz average in the nonexponential category was judged by the examiner, a trained ophthalmic technologist, to have an evident cataract. The data in FIG. 6 indicates that higher total intensities are associated with autocorrelation functions having a second derivative described by equation (12) over some range of τ.

As part of the same study, the examiner visually judged the degree of scattering or scattering status of four locations along the visual axis of each lens. These locations were the anterior, nucleus, posterior, and posterior subcapsular regions. In each region the scattering status was graded on a scale of 0 to 4. For the double exponential functions, the mean value of the scattering status in the posterior cortex was 0.26, while for the autocorrelation functions having a nonexponential component, the mean value was 0.72. A two sample t-test on the difference between these two means yielded a p value of $10^{-6}$, indicating that this difference is indeed statistically significant.

These results provide further indication that greater scattering from the lens is associated with nonexponential correlation functions. The data in FIG. 6 indicates that autocorrelation functions having the form of equation (2) do not produce curves with a fit as precise as desired.

The utility of the autocorrelation function with a nonexponential term is underlined by their dependence on age. This dependence, shown in Table 1 below, gives the proportion of autocorrelation functions with a nonexponential component observed in the same study as the data shown in FIG. 6. Table 1 shows that the proportion of the autocorrelation functions with a nonexponential component increases with age in the posterior cortex of the ocular lens so that nearly 40% of the functions cannot be represented as precisely as desired using equation (2) for the 50- to 60-year-old individuals studied.

TABLE 1

Fraction of non-double exponential correlation functions as a function of age and location

| Age (years) | Anterior | Nucleus | Posterior |
|---|---|---|---|
| 20 to 29 | 0.04 | 0.03 | 0.04 |
| 30 to 39 | 0.02 | 0.02 | 0.15 |
| 40 to 49 | 0.03 | 0.02 | 0.21 |
| 50 to 59 | 0.02 | 0.07 | 0.39 |

In another population of 21 subjects having median age 75 years, about 40% of the correlation functions taken from the lens nucleus were nonexponential. This indicates that the trend found in the posterior cortex, seen in Table 1, can be expected to occur at later ages in the nucleus.

In a related study to the one described above, the changes in the ocular lens were followed for patients undergoing bone marrow transplant therapy, primarily for the treatment of blood cell proliferative diseases. This therapy usually involves the administration of total body irradiation and of high doses of corticosteroids. Both irradiation and steroids are known to be cataractogenic agents. In fact, 48% of the bone marrow transplant patients receiving both irradiation and steroids have been reported to develop posterior subcapsular cataracts within a seven year period. Thus, it is of great interest to study changes in quasielastic light scattering from the ocular lenses of patients following this therapy.

Patients were studied within a one-year period starting just prior to commencement of therapy. An initial visit took place prior to transplant, up to three visits took place within a four-month period after the transplant, and for some patients, a follow-up visit occurred at approximately one year after transplant. At each visit, among other measures, the fraction of autocorrelation functions with a nonexponential component was computed, for each subject and in each location within the lens. Table 2 shows the changes in the average proportion of autocorrelation functions with a nonexponential component observed, for the first three visits after transplant.

TABLE 2

Mean change in fraction of non-double exponential correlation functions with nonexponential component per patient as a function of days post transplant

| Days | Anterior | Nucleus | Posterior |
|---|---|---|---|
| 15–45 | 0.017 (n.s.) | 0.0046 (n.s.) | 0.13* |
| 45–75 | 0.023 (n.s.) | 0.036 (n.s.) | 0.16** |
| 75–105 | 0.034 ∧ | 0.028 (n.s.) | 0.21*** |

∧$p < 0.10$
*$p < 0.01$
**$p < 0.001$
***$p < 0.0001$

These changes were significant in the posterior cortex, as judged by the application of the paired t-test. In particular, there was a mean change of 0.21 in the fraction of non-double exponential correlation functions with a nonexponential component, 75 to 105 days after transplant, in the posterior cortex. The corresponding p-value was less than $10^{-4}$. This increase in the incidence of autocorrelation functions with a nonexponential component is a useful early indicator of the expected, eventual development of cataract in some of these lenses. The term "n.s." indicates that the results are not statistically significant.

QUANTITATIVE MEASURES OF NONEXPONENTIAL CORRELATION FUNCTIONS

As previously discussed, the Durbin-Watson statistic, DW_stat, is used to measure the degree to which the curve is a good fit to the discrete data points. The decreasing values of DW_stat, when computed on residuals from the fit to equation (1) or equation (5) in FIGS. 2B, 3B, 4B, and 5B, indicate increasing evolution towards nonexponential correlation functions. Thus, DW_stat can provide a crude, continuous measure of this evolution, as contrasted with the simple categorization of a function as double exponential or nonexponential. FIGS. 2C, 3C, 5C, and 4C show values of DW_stat corresponding to both double exponential autocorrelation functions and nonexponential autocorrelation functions. These are 2.21 for the double exponential function in FIG. 2A, 1.98 for the double exponential function in FIG. 3A, 0.49 for the nonexponential function in FIG. 5A, and 0.151 for the nonexponential function in FIG. 4A. This illustrates the decrease of DW_stat with increasing nonexponential nature of the autocorrelation functions.

Figure 7:
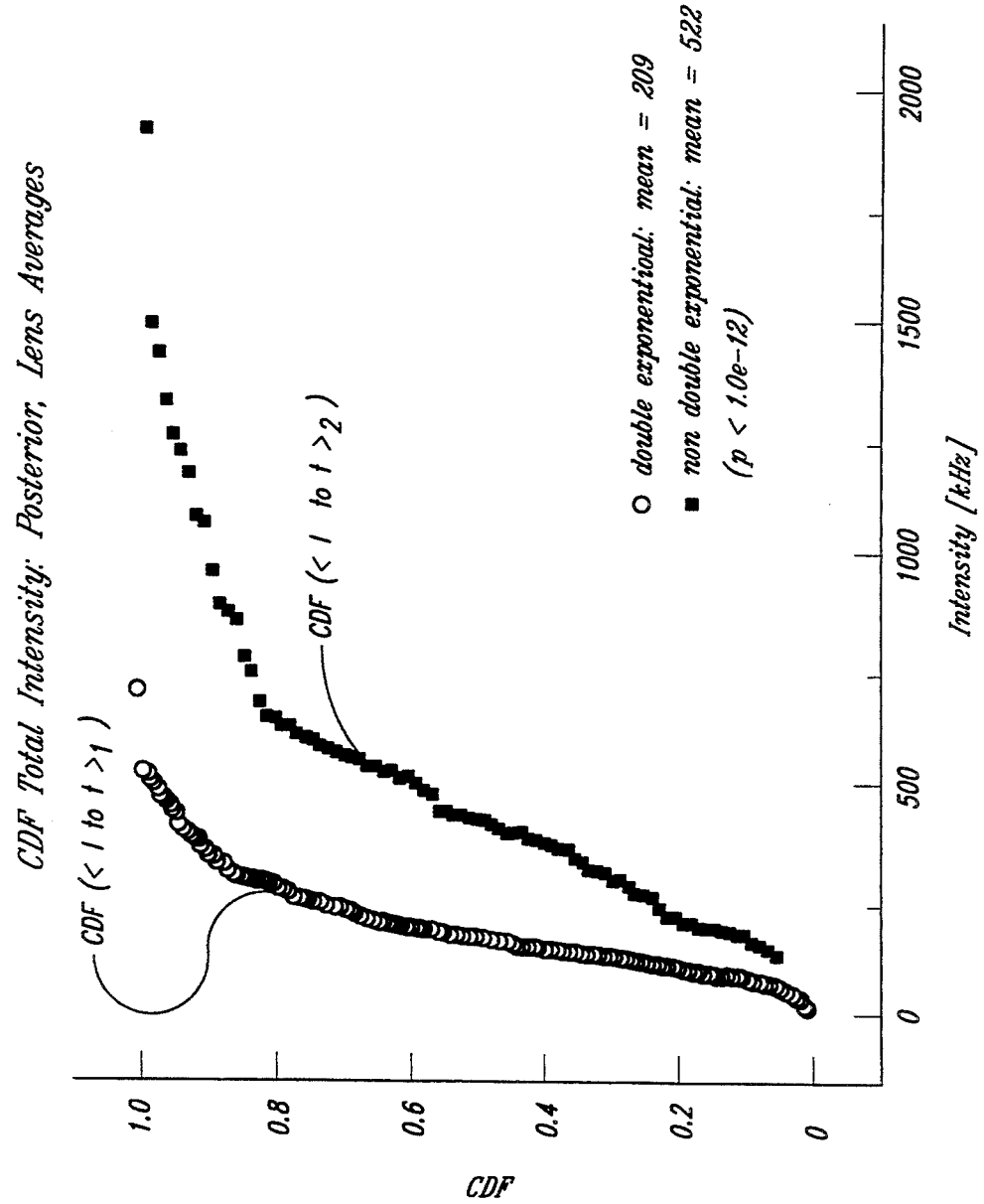
FIG. 7 is a graph of the cumulative density function of the total intensity of scattered light corresponding to double-exponential and nonexponential autocorrelation functions.

FIG. 7 shows the cumulative density function, CDF (<DW_stat>) of the lens average values, <DW_stat>, in the posterior cortex when fitting the discrete data points to a double exponential autocorrelation function having a positive second derivative. An experimenter visually examined the fitted data points and classified the data as either fitting the double exponential autocorrelation function or having a nonexponential form (including a negative second derivative) which precluded a good fit with solely a double exponential function. The mean value of <DW_stat> for the autocorrelation function having nonexponential elements, 1.1, is clearly far below the mean value observed for the double exponential functions, 1.9. Only two average values for double exponential functions lie below <DW_stat> = 1.4, a value above both the median and the mean of the distribution for autocorrelation function with a nonexponential term. These results show the utility of DW_stat as one quantitative measure of the nonexponential correlation functions.

Figure 8:
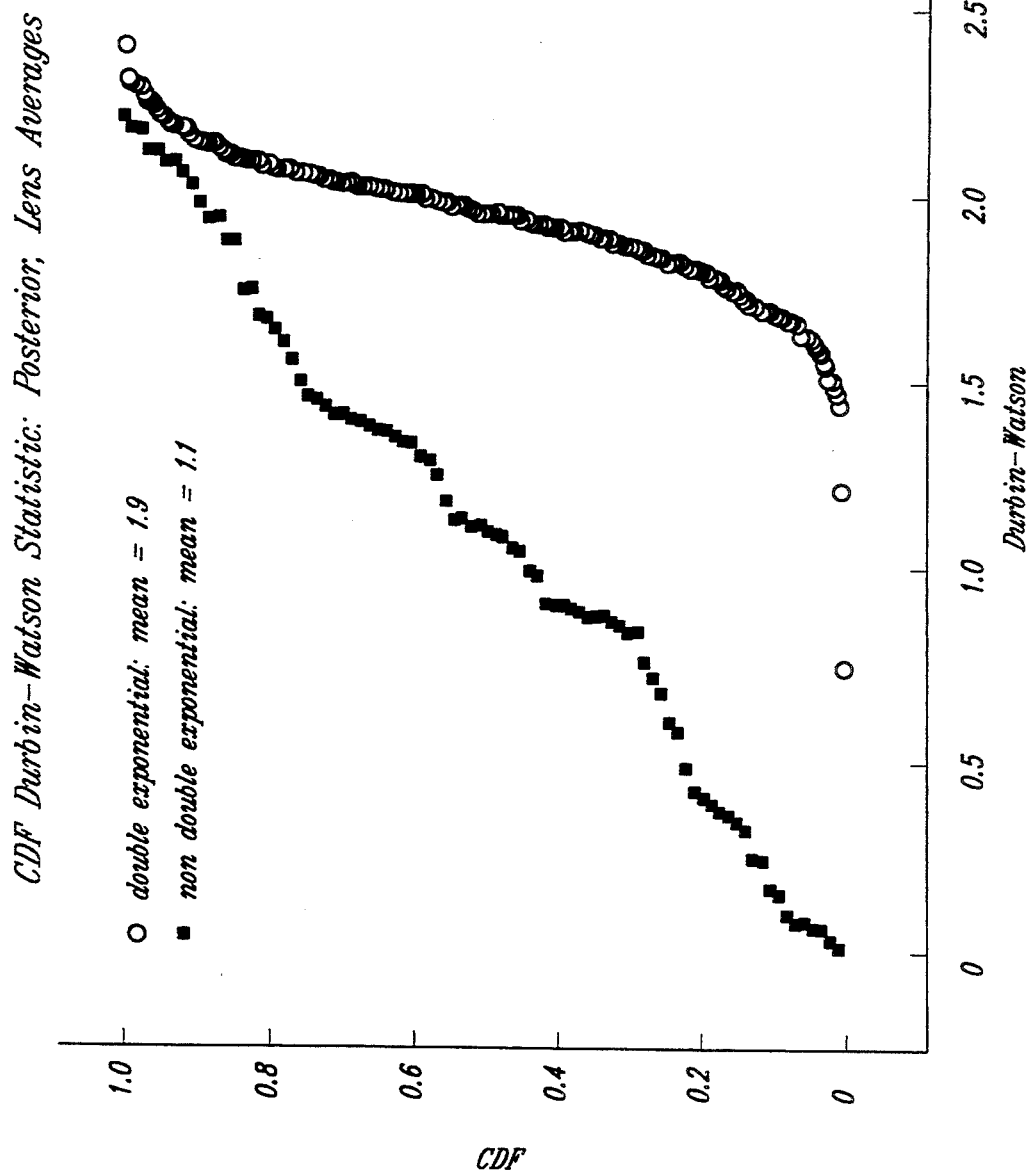
FIG. 8 is a graph of the cumulative density function of the Durbin-Watson statistic corresponding to double-exponential and nonexponential autocorrelation functions.

Changes in DW_stat for the double exponential autocorrelation function were investigated after bone marrow transplant therapy in the study described above. It was found that the mean value of DW_stat in the posterior cortex decreased within the first 120 days post transplant, as compared with the changes in a control group of normal volunteers who did not undergo the transplant therapy. These changes are shown in FIG. 8. The mean change in DW_stat between the initial visit, which occurred prior to transplant for the patients, and subsequent visits, is plotted vertically, and time is plotted horizontally. As can be readily seen in FIG. 8, the decrease in the value of DW_stat for the double exponential autocorrelation function indicates that nonexponential autocorrelation functions appear more frequently as a function of time after irradiation.

Figure 9:
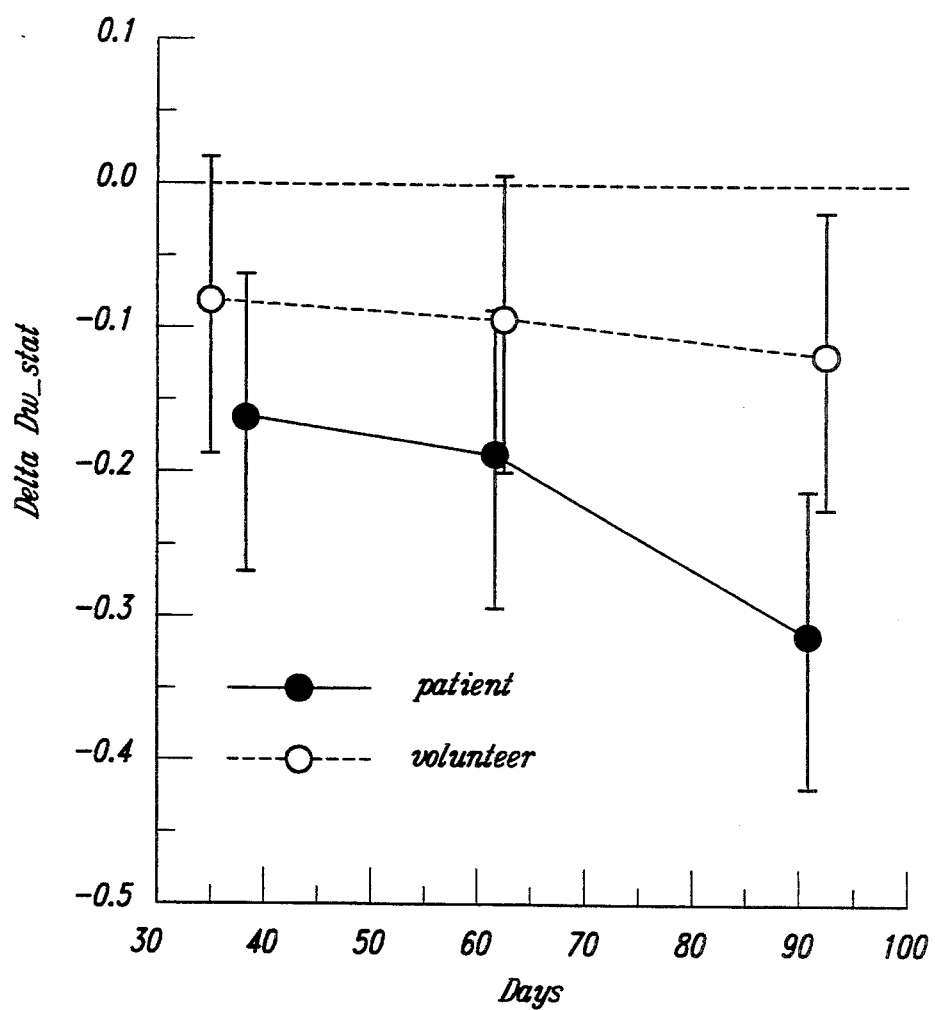
FIG. 9 is a graph of the change in the Durbin-Watson statistic for volunteer subjects and for patients exposed to radiation.

In the same study, it was also found that the changes in DW_stat in the posterior cortex in the first 120 days post transplant were correlated with the observed changes in graded scattering status in the posterior subcapsular region, judged approximately one year post transplant. The scattering status was visually determined by a trained ophthalmic technician using a slit lamp microscope. The scattering status is rated from 0 to 4 with 0 being a clear lens and 4 being a cataractous lens. The scattering status is initially determined before irradiation and again approximately one year after irradiation. This correlation is shown in FIG. 9, in which the changes in scattering status are plotted vertically, and the early changes in DW_stat are plotted horizontally. In FIG. 9, the early changes represent the average of the changes observed for each patient in the visits taking place within 120 days after transplant. The observed correlation is negative, meaning that early decreases in DW_stat are associated with later increases in the scattering status. The correlation coefficient, $R = -0.67$, is statistically significant, with a p-value less than $10^{-4}$. This correlation was further investigated by dropping selected, extreme points, as shown on the plot. The correlations remained significant, with p-values less than 0.005.

These results indicate that DW_stat, and hence the occurrence of nonexponential correlation functions, is useful as an early indicator of subsequent cataractogenesis.

In view of the fact that many of the observed autocorrelation functions using the form of equations (2) and (5) do not produce a curve with a fit as precise as desired, the present invention uses a new functional form of $C(\tau)$, which is capable of fitting nearly all of the observed autocorrelation functions and contains a component that satisfies equation (12) over at least a portion of the range of $\tau$. This functional form of $C(\tau)$ is given by:

$$C(\tau) = \alpha B \left[ (1 - F_{mos})e^{-\frac{\tau}{\tau_f}} + F_{mos}e^{-\frac{\tau}{\tau_s}} \right]^2 + H \cos\left(\frac{2\pi\tau}{\tau_c}\right) + B \quad (13)$$

where $\alpha$ is an amplitude to baseline ratio of the exponential term, B is a baseline value, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, and $\tau_c$, which is in units of time, represents the period of the cosine term and characterizes the correlation time of the nonexponential term. A curve fitting algorithm, such as the least square analysis, determines the optimal values of the parameters of equation (13).

Equation (13) is derived based on a physical model for the influence of natural motion of the eye on the autocorrelation function, as previously discussed. The additional term, $H \cos(2\pi\tau/\tau_c)$, contributes to the correlation function in regions of the lens in which the light scattering is spatially inhomogeneous.

Equation (13) would be expected to apply in cases in which eye motion itself has an exponential dependence of the autocorrelation of the scattering volume identity on delay time. In this case, the interpretation of some parameters would be changed as shown in equation (14) below:

$$C(\tau) = \alpha B \left[ (1 - F_s)e^{-\frac{\tau}{\tau_f}} + F_s e^{-\frac{\tau}{\tau_s}} \right]^2 + H \cos\left(\frac{2\pi\tau}{\tau_c}\right) + B \quad (14)$$

where $\alpha$ is an amplitude to baseline ratio, B is a baseline value, t is a time delay variable, $\tau_f$ is a fast correlation time, $\tau_s$ is a slow correlation time, $F_s$ is a dimensionless parameter characterizing the relative proportion of the correlation function associated with fast correlation times and slow correlation times, H is an amplitude parameter of the nonexponential term, and $\tau_c$, which is in units of time, represents the period of the cosine term and characterizes the correlation time of the nonexponential term.

Figure 10:
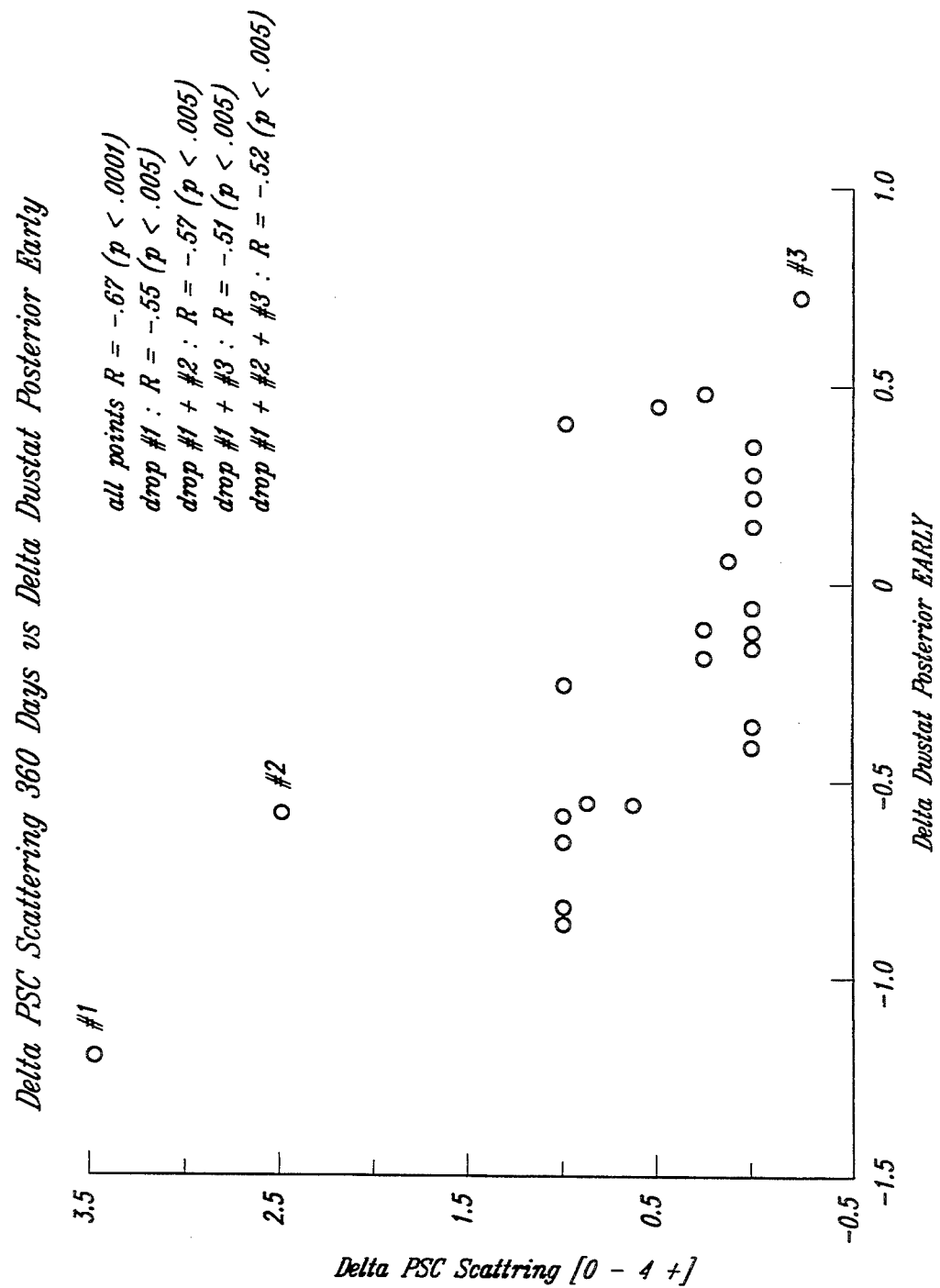
FIG. 10 is a graph of the change in posterior subcapsular region scattering one year after irradiation versus the early change in the Durbin-Watson statistic.

Examples of correlation functions well fit by equation (13) or by a corresponding normalized form without the baseline are shown in FIGS. 10A, 11A and 12A. As seen in FIG. 10A, a curve, $C_{fit}(\tau)$, indicated by the reference numeral 76, is derived from the discrete data points 78 using the curve fitting program and the autocorrelation function of equation (13) or by a corresponding normalized form without the baseline. The residual data, shown in FIG. 10B, is randomly distributed about zero. The statistics of FIG. 10C show a DW_stat of 1.76, indicating that the curve 76 is a good fit to the autocorrelation function of equation (13).

Similarly, a curve, $C_{fit}(\tau)$, indicated by the reference numeral 82 in FIG. 11A, is derived from the discrete data points 84 using the curve fitting program and the autocorrelation function of equation (13). As seen in the residual data of FIG. 11B and the statistics of FIG. 11C, the curve 82 is a good fit to the autocorrelation function of equation (13). The residual data is randomly distributed about zero, and the DW_stat is 2.36. A curve, $C_{fit}(\tau)$, indicated by the reference numeral 86 in FIG. 12A, is derived from the discrete data points 88 using the curve fitting program and the autocorrelation function of the autocorrelation function of equation (13). As seen in the residual data of FIG. 12B and the statistics of FIG. 12C, the curve 86 is a good fit to equation (13). The residual data is randomly distributed about zero, and the DW_stat is 1.60. Thus, the autocorrelation function of equation (13) is shown to provide reliable results for a variety of patients.

In a recent study, equation (13) has proven capable of giving good fits to all of the 103 samples obtained in the study. Forty-two of these functions were nonexponential as indicated by a nonzero value for H, the magnitude of the oscillatory cosine term. Note that with H=0, equation (13) reduces to the previous double exponential model illustrated in equation (5). These results indicate the utility of the additional parameters, H and $\tau_c$, in characterizing light scattering from the ocular lens in vivo. This study demonstrates that equation (13) can be used to reliably fit nonexponential functions found in patients.

In operation, the apparatus 10 (see FIG. 1) uses the laser 14 to produce the substantially monochromatic, coherent, collimated light. Standard optics 18 are used to cause the laser light to impinge on the ocular tissue 12. Light is scattered by molecular constituents within the ocular tissue 12. A portion of the incident light 24 is scattered by the ocular tissue along the direction 22 and is collected by the fiber optic 30 and delivered to the light detector 32. The light detector 32 converts the light signals into an electrical signal. The electrical signal is amplified by the amplifier-discriminator 36 and delivered to the autocorrelator 38. The autocorrelator 38 determines the discrete data points 78 (see FIG. 10A). A computer (not shown) uses the curve fitting program and the autocorrelation function of equation (13) to fit the discrete data points to a curve 76. The computer also calculates the residuals and the DW_stat value. Preliminary research indicates that the value of the amplitude factor, H, may be used to determine the degree of cataractogenesis. Thus, the present invention is capable of providing early clinical indications of cataractogenesis in a population of subjects for whom prior art techniques were unreliable.

Those skilled in the art will recognize, or be able to ascertain, using no more than routine experimentation, many equivalents to the specific embodiment of the invention described herein. For example, the delivery, observation, control and collection optics are not intended to be solely limited to the embodiments described herein, but rather are intended to extend to any optical system suitable for these purposes. Similarly, other mathematical measures of a negative second derivative of the autocorrelation function $C(\tau)$ may be constructed, as alternatives to that given in equation (13).

For one example, one may expand the cosine term in equation (13) in a power series in $\tau$ near $\tau=0$, and use instead the resulting form $H(1-(\frac{1}{2})(2\pi/\tau c)^2\tau^2+ \ldots )$ in place of the cosine term, to fit the data together with the remaining exponential terms.

For another example, one may incorporate the possibility of immobile scatterers into the original correlation function, as disclosed in pending U.S. Pat. No. 5,279,296.

For another example, one may use numerical means of detecting the presence of and quantitating the magnitude of elements of the observed autocorrelation function which exhibit a non-positive second derivative. This could be done, for example, by evaluating numerically from the discrete data points the value of the second derivative of the $C(\tau)$ or of the residuals $R(\tau)$ as a function of $\tau$ over a selected range or ranges of $\tau$. Such equivalents are intended to be encompassed by the following claims.

What is claimed is:

1. A method for in vivo detection of cataractogenesis in ocular tissue, comprising the steps of:
    (a) producing a light;
    (b) causing said light to impinge on the ocular tissue;
    (c) collecting light that is scattered from the ocular tissue;
    (d) performing a correlation analysis on said collected light and producing a signature having a component whose second derivative is less than or equal to zero; and
    (e) detecting cataractogenesis from said signature.

2. The method of claim 1 wherein said signature contains at least one sinusoidal term.

3. The method of claim 2 wherein said sinusoidal term contains an amplitude component, the method further including the step of determining said amplitude component.

4. The method of claim 1 wherein said signature contains an exponential component and a nonexponential component.

5. The method of claim 4 wherein said nonexponential component contains an amplitude component, the method further including the step of determining said amplitude component.

6. The method of claim 1 wherein step (c) comprises collecting the light that is scattered from the ocular tissue over a time period and step (d) comprises computing a temporal autocorrelation function of the collected light.

7. The method of claim 6 wherein said step (a) produces a substantially monochromatic, coherent light, step (d) further comprises performing an analysis on said temporal autocorrelation function to determine the optimal values of the parameters of the function $C(\tau)$ which best fits said temporal autocorrelation function, where $$C(\tau) = \alpha B \left[ (1 - F_{mos})e^{-\frac{\tau}{\tau_f}} + F_{mos}e^{-\frac{\tau}{\tau_s}} \right]^2 + H\cos\left(\frac{2\pi\tau}{\tau_c}\right) + B,$$

where $\alpha$ is an amplitude to baseline ratio of the exponential term, B is a baseline value, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, and $\tau_c$, which is in units of time, represents the period of the cosine term and characterizes the correlation time of the nonexponential term.

8. The method of claim 6 wherein step (d) further comprises performing an analysis on said temporal autocorrelation function to determine the optimal values of the parameters of the function $C(\tau)$ which best fits said temporal autocorrelation function, where $$C(\tau) = \alpha B \left[ (1 - F_S)e^{-\frac{\tau}{\tau_f}} + F_S e^{-\frac{\tau}{\tau_s}} \right]^2 + H\cos\left(\frac{2\pi\tau}{\tau_c}\right) + B,$$

where $\alpha$ is an amplitude to baseline ratio, B is a baseline value, $\tau$ is a time delay variable, $\tau_f$ is a fast correlation time, $\tau_s$ is a slow correlation time, $F_S$ is a dimensionless parameter characterizing the relative proportion of the correlation function associated with fast correlation times and slow correlation times, H is an amplitude parameter of the nonexponential term, and $\tau_c$, which is in units of time, represents the period of the cosine term and characterizes the correlation time of the nonexponential term.

9. A method for in vivo detection of cataractogenesis in ocular tissue, comprising the steps of:
    (a) producing a light;
    (b) causing said light to impinge on the ocular tissue;
    (c) collecting light that is scattered from the ocular tissue;
    (d) performing an autocorrelation analysis on the collected light and determining a signature having a component whose second derivative is less than or equal to zero; and
    (e) detecting cataractogenesis from said signature.

10. The method of claim 9 wherein said signature contains at least one sinusoidal term.

11. The method of claim 10 wherein said sinusoidal term contains an amplitude component, the method further including the step of determining said amplitude component.

12. The method of claim 9 wherein said signature contains an exponential component and a nonexponential component.

13. The method of claim 12 wherein said nonexponential component contains an amplitude component, the method further including the step of determining said amplitude component.

14. The method of claim 9 wherein said step (a) produces a substantially monochromatic, coherent light, step (d) comprises performing an analysis on the temporal autocorrelation function to determine the optimal values of the parameters of the function $C(\tau)$ which best fits the temporal autocorrelation function, where $$C(\tau) = \alpha B \left[ (1 - F_{mos})e^{-\frac{\tau}{\tau_f}} + F_{mos}e^{-\frac{\tau}{\tau_s}} \right]^2 + H\cos\left(\frac{2\pi\tau}{\tau_c}\right) + B,$$

where $\alpha$ is an amplitude to baseline ratio of the exponential term, B is a baseline value, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, and $\tau_c$, which is in units of time, represents the period of the cosine term and characterizes the correlation time of the nonexponential term.

15. The method of claim 9 wherein step (d) further comprises performing an analysis on the temporal autocorrelation function to determine the optimal values of the parameters of the function $C(\tau)$ which best fits the temporal autocorrelation function, where $$C(\tau) = \alpha B \left[ (1 - F_s)e^{-\frac{\tau}{\tau_f}} + F_s e^{-\frac{\tau}{\tau_s}} \right]^2 + H \cos\left(\frac{2\pi\tau}{\tau_c}\right) + B,$$

where $\alpha$ is an amplitude to baseline ratio, B is a baseline value, $\tau$ is a time delay variable, $\tau_f$ is a fast correlation time, $\tau_s$ is a slow correlation time, $F_s$ is a dimensionless parameter characterizing the relative proportion of the correlation function associated with fast correlation times and slow correlation times, H is an amplitude parameter of the nonexponential term, and $\tau_c$, which is in units of time, represents the period of the cosine term and characterizes the correlation time of the nonexponential term.

16. A method for in vivo detection of cataractogenesis in ocular tissue, comprising the steps of:
   (a) producing a light;
   (b) causing said light to impinge on the ocular tissue;
   (c) collecting light that is scattered from the ocular tissue;
   (d) performing an autocorrelation analysis on the collected light and determining a signature having an exponential component and a nonexponential component; and
   (e) detecting cataractogenesis from said signature.

17. The method of claim 16 wherein said signature has a component whose second derivative is less than or equal to zero.

18. The method of claim 16 wherein said nonexponential component contains at least one sinusoidal term.

19. The method of claim 18 wherein said sinusoidal term contains an amplitude component, the method further including the step of determining said amplitude component.

20. The method of claim 16 wherein said nonexponential component contains an amplitude component, the method further including the step of determining said amplitude component.

21. The method of claim 16 wherein said step (a) produces a substantially monochromatic, coherent light, step (d) comprises performing an analysis on the temporal autocorrelation function to determine the optimal values of the parameters of the function $C(\tau)$ which best fits the temporal autocorrelation function, where $$C(\tau) = \alpha B \left[ (1 - F_{mos})e^{-\frac{\tau}{\tau_f}} + F_{mos} e^{-\frac{\tau}{\tau_s}} \right]^2 +$$

$$H \cos\left(\frac{2\pi\tau}{\tau_c}\right) + B,$$

where $\alpha$ is an amplitude to baseline ratio of the exponential term, B is a baseline value, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, and $\tau_c$, which is in units of time, represents the period of the cosine term and characterizes the correlation time of the nonexponential term.

22. The method of claim 16 wherein step (d) further comprises performing an analysis on the temporal autocorrelation function to determine the optimal values of the parameters of the function $C(\tau)$ which best fits the temporal autocorrelation function, where $$C(\tau) = \alpha B \left[ (1 - F_s)e^{-\frac{\tau}{\tau_f}} + F_s e^{-\frac{\tau}{\tau_s}} \right]^2 + H \cos\left(\frac{2\pi\tau}{\tau_c}\right) + B,$$

where $\alpha$ is an amplitude to baseline ratio, B is a baseline value, $\tau$ is a time delay variable, $\tau_f$ is a fast correlation time, $\tau_s$ is a slow correlation time, $F_s$ is a dimensionless parameter characterizing the relative proportion of the correlation function associated with fast correlation times to slow correlation times, H is an amplitude parameter of the nonexponential term, and $\tau_c$, which is in units of time, represents the period of the cosine term and characterizes the correlation time of the nonexponential term.

23. A method for in vivo detection of cataractogenesis in ocular tissue wherein a light source is directed to impinge on the ocular tissue, the method comprising the steps of:
   (a) collecting light that is scattered from the ocular tissue; and
   (b) performing a correlation analysis on said collected light and producing a signature indicative of cataractogenesis, said signature having a component whose second derivative is less than or equal to zero.

24. Apparatus for in vivo detection of cataractogenesis in ocular tissue, comprising:
   light means for directing a light to impinge on the ocular tissue;
   a light collector constructed to collect light that is scattered from the ocular tissue and generate a signal indicative of an intensity of said collected light;
   correlation electrical circuitry constructed to receive said signal and perform a correlation analysis on said collected light to determine a signature having a component whose second derivative is less than or equal to zero; and
   detection electrical circuitry electrically coupled to said correlation electrical circuitry to detect cataractogenesis from said signature.

25. The apparatus of claim 24 wherein said correlation electrical circuitry is further constructed to determine said signature with at least one sinusoidal term containing an amplitude component, said correlation electrical circuitry determining said amplitude component.

26. The apparatus of claim 24 wherein said correlation electrical circuitry is further constructed to determine said signature with an exponential component and a nonexponential component, said nonexponential component containing an amplitude component, said correlation electrical circuitry determining said amplitude component.

27. The apparatus of claim 24 wherein said light collector collects light that is scattered from the ocular tissue over a time period and said correlation electrical circuitry comprises a computer programmed to compute a temporal autocorrelation function of the intensity of the collected light.

28. The apparatus of claim 24 wherein said light collector collects light that is scattered from the ocular tissue over a time period and said correlation electrical circuitry comprises an integrated circuit for computing a temporal autocorrelation function of the intensity of the collected light.

29. The apparatus of claim 24 wherein said light collector collects light that is scattered from the ocular tissue over a time period and said correlation electrical circuitry comprises a standalone autocorrelator for computing a temporal autocorrelation function of the intensity of the collected light.

30. The apparatus of claim 24 wherein said light means provides a substantially monochromatic, coherent light, said correlation electrical circuitry comprises means for analyzing a temporal autocorrelation function to determine the optimal values of the parameters of the function $C(\tau)$ which best fits said temporal autocorrelation function, where $$C(\tau) = \alpha B \left[ (1 - F_{mos})e^{-\frac{\tau}{\tau_f}} + F_{mos}e^{-\frac{\tau}{\tau_s}} \right]^2 + H\cos\left(\frac{2\pi\tau}{\tau_c}\right) + B,$$

where $\alpha$ is an amplitude to baseline ratio of the exponential term, B is a baseline value, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, and $\tau_c$, which is in units of time, represents the period of the cosine term and characterizes the correlation time of the nonexponential term.

31. The apparatus of claim 24 wherein said correlation electrical circuitry comprises means for analyzing a temporal autocorrelation function to determine the optimal values of the parameters of the function $C(\tau)$ which best fits said temporal autocorrelation function, where $$C(\tau) = \alpha B \left[ (1 - F_s)e^{-\frac{\tau}{\tau_f}} + F_s e^{-\frac{\tau}{\tau_s}} \right]^2 + H\cos\left(\frac{2\pi\tau}{\tau_c}\right) + B,$$

where $\alpha$ is an amplitude to baseline ratio, B is a baseline value, $\tau$ is a time delay variable, $\tau_f$ is a fast correlation time, $\tau_s$ is a slow correlation time, $F_s$ is a dimensionless parameter characterizing the relative proportion of the correlation function associated with fast correlation times and slow correlation times, H is an amplitude parameter of the nonexponential term, and $\tau_c$, which is in units of time, represents the period of the cosine term and characterizes the correlation time of the nonexponential term.

32. The apparatus of claim 24 wherein said light means includes a laser.

33. Apparatus for in vivo detection of cataractogenesis in ocular tissue, comprising:

light means for directing a light to impinge on the ocular tissue;
means for collecting light that is scattered from the ocular tissue;
correlation means for performing a correlation analysis on the collected light and determining a signature having a component whose second derivative is less than or equal to zero; and
means for determining a degree of cataractogenesis from said signature.

34. The apparatus of claim 33 wherein said correlation means comprises a computer programmed to compute a temporal autocorrelation function of the intensity of the collected light.

35. The apparatus of claim 33 wherein said correlation means comprises an integrated circuit for computing a temporal autocorrelation function of the intensity of the collected light.

36. The apparatus of claim 33 wherein said correlation means comprises a standalone autocorrelator for computing a temporal autocorrelation function of the intensity of the collected light.

37. The apparatus of claim 33 wherein said correlation means analyzes a temporal autocorrelation function to determine the optimal values for the parameters of the function $C(\tau)$ which best fits the temporal autocorrelation function, where $$C(\tau) = \alpha B \left[ (1 - F_{mos})e^{-\frac{\tau}{\tau_f}} + F_{mos}e^{-\frac{\tau}{\tau_s}} \right]^2 + H\cos\left(\frac{2\pi\tau}{\tau_c}\right) + B,$$

where $\alpha$ is an amplitude to baseline ratio of the exponential term, B is a baseline value, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, and $\tau_c$, which is in units of time, represents the period of the cosine term and characterizes the correlation time of the nonexponential term.

38. The apparatus of claim 33 wherein said correlation means analyzes a temporal autocorrelation function to determine the optimal values for the parameters of the function $C(\tau)$ which best fits the temporal autocorrelation function, where $$C(\tau) = \alpha B \left[ (1 - F_s)e^{-\frac{\tau}{\tau_f}} + F_s e^{-\frac{\tau}{\tau_s}} \right]^2 + H\cos\left(\frac{2\pi\tau}{\tau_c}\right) + B,$$

where $\alpha$ is an amplitude to baseline ratio, B is a baseline value, $\tau$ is a time delay variable, $\tau_f$ is a fast correlation time, $\tau_s$ is a slow correlation time, $F_s$ is a dimensionless parameter characterizing the relative proportion of the correlation function associated with fast correlation times to slow correlation times, H is an amplitude parameter of the nonexponential term, and $\tau_c$, which is in units of time, represents the period of the cosine term and characterizes the correlation time of the nonexponential term.

39. The apparatus of claim 33 wherein said light means includes a laser.

* * * * *

UNITED STATES PATENT AND TRADEMARK OFFICE
CERTIFICATE OF CORRECTION

PATENT NO. : 5,427,094
DATED : June 27, 1995
INVENTOR(S) : George M. Thurston, et al It is certified that error appears in the above-indentified patent and that said Letters Patent is hereby corrected as shown below:

Column 1, line 4, insert:

--*This invention was made with government support under Grant No. NIH-5R01-EY05127 by the National Institutes of Health. The government has certain rights in the invention.*--

Signed and Sealed this

Sixteenth Day of April, 1996

Attest:

BRUCE LEHMAN

*Attesting Officer*  *Commissioner of Patents and Trademarks*